(12) United States Patent
Gateno

(10) Patent No.: US 12,207,850 B2
(45) Date of Patent: Jan. 28, 2025

(54) CUSTOMIZABLE HELICAL TELESCOPING INTERNAL CRANIOFACIAL DISTRACTOR

(71) Applicant: THE METHODIST HOSPITAL SYSTEM, Houston, TX (US)

(72) Inventor: Jaime Gateno, Bellaire, TX (US)

(73) Assignee: THE METHODIST HOSPITAL SYSTEM, Houston, TX (US)

( * ) Notice: Subject to any disclaimer, the term of this patent is extended or adjusted under 35 U.S.C. 154(b) by 767 days.

(21) Appl. No.: 17/298,171

(22) PCT Filed: Nov. 27, 2019

(86) PCT No.: PCT/US2019/063680
§ 371 (c)(1),
(2) Date: May 28, 2021

(87) PCT Pub. No.: WO2020/113055
PCT Pub. Date: Jun. 4, 2020

(65) Prior Publication Data
US 2022/0096134 A1     Mar. 31, 2022

Related U.S. Application Data

(60) Provisional application No. 62/773,837, filed on Nov. 30, 2018.

(51) Int. Cl.
*A61B 17/80* (2006.01)
*A61B 17/66* (2006.01)
(Continued)

(52) U.S. Cl.
CPC ...... *A61B 17/8019* (2013.01); *A61B 17/8071* (2013.01); *A61B 34/10* (2016.02);
(Continued)

(58) Field of Classification Search
CPC ............ A61B 17/8019; A61B 17/8071; A61B 17/666; A61B 17/663; A61B 17/66;
(Continued)

(56) References Cited

U.S. PATENT DOCUMENTS

RE14,291 E  *  4/1917  Wegener ................... 411/941
5,662,649 A      9/1997  Huebner
(Continued)

FOREIGN PATENT DOCUMENTS

CN          203263516 U      6/2013

OTHER PUBLICATIONS

International Search Report and Written Opinion in PCT/US2019/063680. mailed Mar. 5, 2020. 15 pages.
(Continued)

*Primary Examiner* — Tracy L Kamikawa
(74) *Attorney, Agent, or Firm* — Meunier Carlin & Curfman LLC

(57) ABSTRACT

The present disclosure is directed to a customizable distractor for oral and maxillofacial surgery and a system and method for designing and making the same. The distractor includes a steering apparatus that is movable along the helical-shaped distraction path to create gap between the first and second bone segments, an anchoring member for coupling the steering apparatus a first and second bone segment, and a distraction drive mechanism is used to drive movement of the steering apparatus along the distraction path.

27 Claims, 40 Drawing Sheets

(51) Int. Cl.
*A61B 34/10* (2016.01)
*A61B 90/00* (2016.01)
*A61B 17/00* (2006.01)
*A61B 17/56* (2006.01)
*A61B 34/00* (2016.01)

(52) U.S. Cl.
CPC .............. *A61B 90/03* (2016.02); *A61B 90/37* (2016.02); *A61B 2017/00991* (2013.01); *A61B 2017/568* (2013.01); *A61B 2034/105* (2016.02); *A61B 2034/108* (2016.02); *A61B 2034/254* (2016.02); *A61B 2090/035* (2016.02); *A61B 2090/3762* (2016.02)

(58) Field of Classification Search
CPC ..... A61B 17/8866; A61B 34/10; A61B 90/03; A61B 90/37; A61B 2034/105; A61B 2034/108; A61B 2034/254; A61B 2090/035; A61B 2090/3762; A61B 2017/00991; A61B 2017/568
See application file for complete search history.

(56) References Cited

U.S. PATENT DOCUMENTS

| | | | |
|---|---|---|---|
| 5,700,263 | A | 12/1997 | Schendel |
| 6,139,316 | A * | 10/2000 | Sachdeva ................. A61C 7/10 433/7 |
| 8,282,635 | B1 | 10/2012 | Amato |
| 8,808,290 | B2 | 8/2014 | Dubois |
| 2007/0162045 | A1 | 7/2007 | Ahmed |
| 2014/0324046 | A1 * | 10/2014 | Vicatos ................. A61B 17/663 606/58 |
| 2014/0378983 | A1 | 12/2014 | Noon et al. |
| 2015/0272644 | A1 | 10/2015 | Noon et al. |
| 2017/0296249 | A1 | 10/2017 | Walker et al. |
| 2018/0360497 | A1 | 12/2018 | Strozyk et al. |

OTHER PUBLICATIONS

Extended European Search Report issued for Application No. 19889441.2, dated Jul. 28, 2022.
McCarthy JG, Schreiber J, Karp N, Thorne CH, Grayson BH. Lengthening the human mandible by gradual distraction. Plast Reconstr Surg 1992;89:1-8; discussion 9-10.
Rachmiel A, Potparic Z, Jackson IT, et al. Midface advancement by gradual distraction. British journal of plastic surgery 1993;46:201-7.
Block MS, Brister GD. Use of distraction osteogenesis for maxillary advancement: preliminary results. Journal of oral and maxillofacial surgery : official journal of the American Association of Oral and Maxillofacial Surgeons 1994;52:282-6; discussion 7-8.
Altuna G, Walker DA, Freeman E. Surgically assisted rapid orthodontic lengthening of the maxilla in primates—a pilot study. Am J Orthod Dentofacial Orthop 1995;107:531-6.
Altuna G, Walker DA, Freeman E. Surgically assisted-rapid orthopedic lengthening of the maxilla in primates—relapse following distraction osteogenesis. The International journal of adult orthodontics and orthognathic surgery 1995;10:269-75.
Block MS, Cervini D, Chang A, Gottsegen GB. Anterior maxillary advancement using tooth-supported distraction osteogenesis. Journal of oral and maxillofacial surgery : official journal of the American Association of Oral and Maxillofacial Surgeons 1995;53:561-5.

Cohen SR, Boydston W, Hudgins R, Burstein FD. Monobloc and facial bipartition distraction with internal devices. J Craniofac Surg 1999;10:244-51.
Matsumoto K, Nakanishi H, Seike T, Shinno K, Hirabayashi S. Application of the distraction technique to scaphocephaly. J Craniofac Surg 2000;11:172-6.
Nadal E, Dogliotti PL, Rodriguez JC, Zuccaro G. Craniofacial distraction osteogenesis en bloc. J Craniofac Surg 2000;11:246-51; discussion 52-3.
Molina F, Ortiz Monasterio F. Mandibular elongation and remodeling by distraction: a farewell to major osteotomies. Plast Reconstr Surg 1995;96:825-40; discussion 41-2.
Verlinden CR, van de Vijfeijken SE, Jansma EP, Becking AG, Swennen GR. Complications of mandibular distraction osteogenesis for congenital deformities: a systematic review of the literature and proposal of a new classification for complications. Int J Oral Maxillofac Surg 2015;44:37-43.
Verlinden CR, van de Vijfeijken SE, Tuinzing DB, Becking AG, Swennen GR. Complications of mandibular distraction osteogenesis for acquired deformities: a systematic review of the literature. Int J Oral Maxillofac Surg 2015;44:956-64.
Verlinden CR, van de Vijfeijken SE, Tuinzing DB, Jansma EP, Becking AG, Swennen GR. Complications of mandibular distraction osteogenesis for developmental deformities: a systematic review of the literature. Int J Oral Maxillofac Surg 2015;44:44-9.
Gateno J, Kim KW, Lalani Z, et al. Biomechanical evaluation of the pins of a mandibular external distractor. Journal of oral and maxillofacial surgery : official journal of the American Association of Oral and Maxillofacial Surgeons 2004;62:1259-63.
Ritter L, Yeshwant K, Seldin EB, et al. Range of curvilinear distraction devices required for treatment of mandibular deformities. Journal of oral and maxillofacial surgery : official journal of the American Association of Oral and Maxillofacial Surgeons 2006;64:259-64.
Yeshwant KC, Thurmuller P, Seldin EB. Geometric considerations in the transition from two-dimensional to three-dimensional treatment planning. Atlas Oral Maxillofac Surg Clin North Am 2005;13:13-23.
Samchukov, Mikhail L., Jason B. Cope, and Alexander M. Cherkashin. "The effect of sagittal orientation of the distractor on the biomechanics of mandibular lengthening." Journal of oral and maxillofacial surgery 57.10 (1999): 1214-1221.
Baroon, Jasem, and Bahram Ravani. "Three-dimensional generalizations of Reuleaux's and Instant center methods based on line geometry." (2010): 041011.
Zhao, Liang, et al. "Biomechanical analysis of a curvilinear distractor device for correcting mandibular symphyseal defects." Journal of Oral and Maxillofacial Surgery 72.6 (2014): 1158-1167.
Lu, Songhe, et al. "Biomechanical optimization of the diameter of distraction screw in distraction implant by three-dimensional finite element analysis." Computers in biology and medicine 43.11 (2013): 1949-1954.
Robinson, Randolph C., Patrick J. O'Neal, and Ginger H. Robinson. "Mandibular distraction force: laboratory data and clinical correlation." Journal of oral and maxillofacial surgery 59.5 (2001): 539-544.
Dorafshar, Amir H., et al. "Found in space: computer-assisted orthognathic alignment of a total face allograft in six degrees of freedom." Journal of Oral and Maxillofacial Surgery 72.9 (2014): 1788-1800.
Kaban, Leonard B., et al. "Clinical application of curvilinear distraction osteogenesis for correction of mandibular deformities." Journal of oral and maxillofacial surgery 67.5 (2009): 996-1008.

* cited by examiner

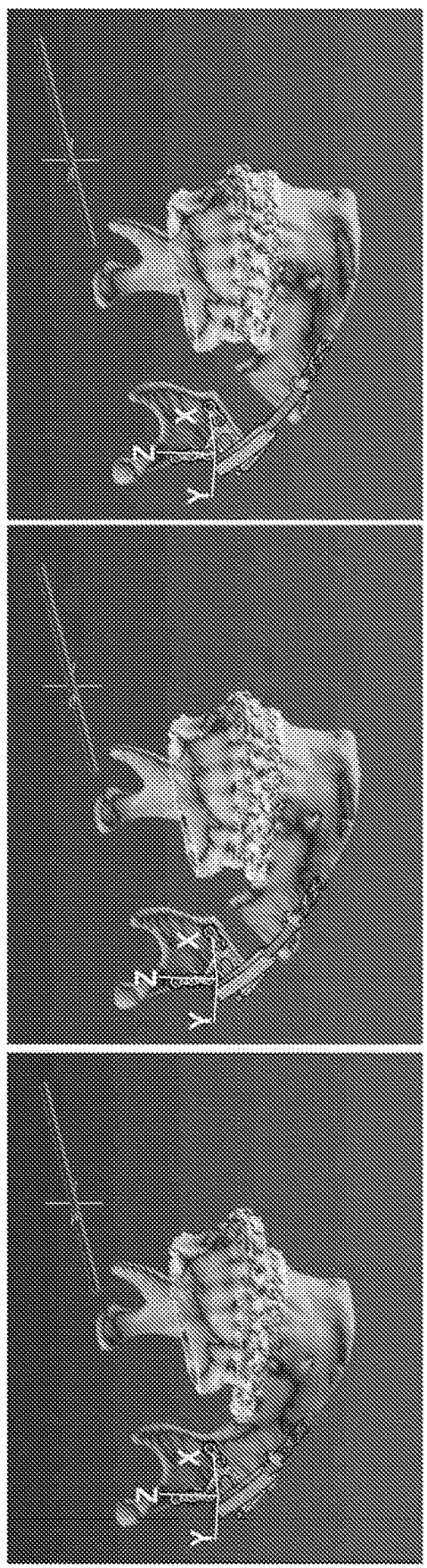

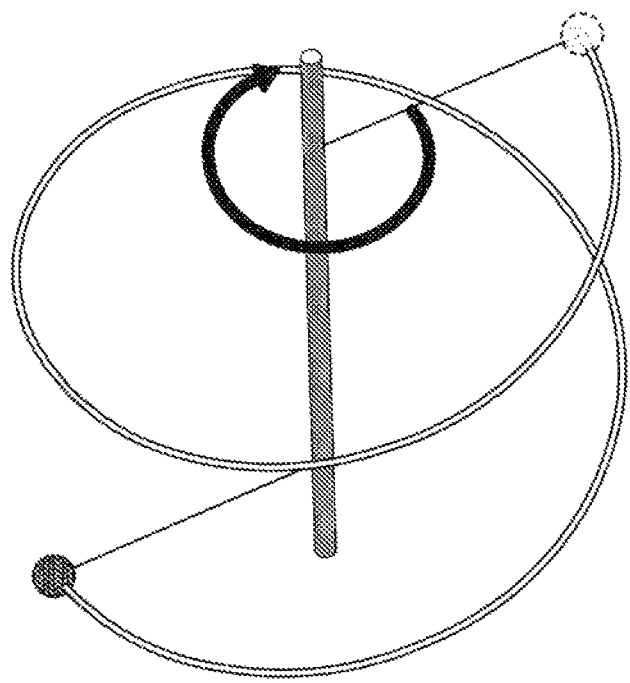
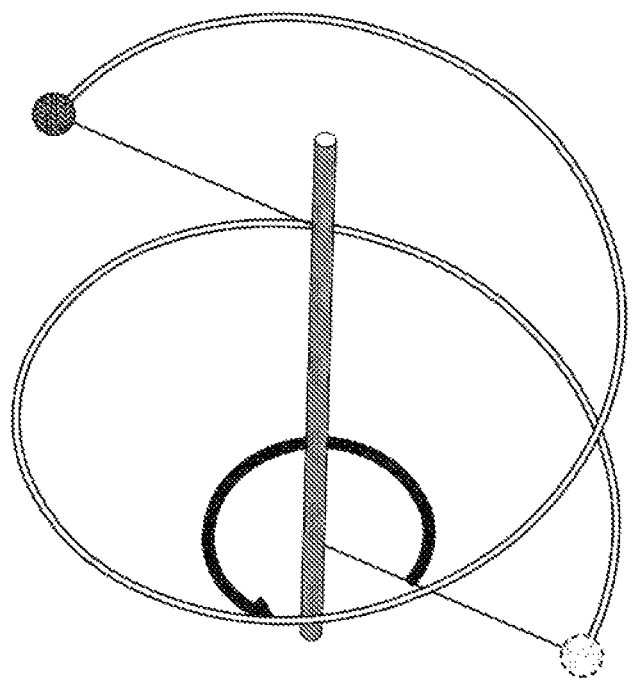
FIG. 6

[Worm-rack drive]

| Parametrize | | X | Y | Z |
|---|---|---|---|---|
| | P1 | -45.7 | 117.4 | 62.3 |
| | P2 | -0.2 | 61 | 49.1 |
| | P3 | 47 | 114.1 | 60.8 |
| | P1 | -44.3 | 102.8 | 50.2 |
| Final Pose | P2 | -0.8 | 43.5 | 50.2 |
| | P3 | 48.1 | 96.3 | 47.9 |

Spiral Motion Parameters

| | | | |
|---|---|---|---|
| Axis unit direction | -0.988283 | 0.0878715 | -0.124798 |
| Axis point | 34.002 | 53.1633 | 124.997 |
| Translation distance | -1.04132 | | |
| Rotation angle | 14.1166 | | |
| Pitch | -4.22647 | | |

Parametrize     Reset

FIG. 35

CUSTOMIZABLE HELICAL TELESCOPING INTERNAL CRANIOFACIAL DISTRACTOR

CROSS-REFERENCE TO RELATED APPLICATIONS

This application is a national stage application filed under 35 U.S.C. § 371 of PCT/US2019/063680 filed Nov. 27, 2019, which claims the benefit of U.S. provisional patent application No. 62/773,837, filed on Nov. 30, 2018, the disclosures of which are expressly incorporated herein by reference in their entireties.

TECHNICAL FIELD

This invention relates generally to a customizable distractor for craniofacial surgery.

BACKGROUND OF THE INVENTION

Distraction osteogenesis is a surgical technique for lengthening short bones to repair skeletal deformities and in reconstructive surgery. A distraction osteogenesis procedure begins with a surgeon cutting the deformed bone (osteotomy) and stabilizing the bone segments in their original position. The bone segments are stabilized in their original alignment with a special orthopedic device called distractor. The wound(s) are then allowed to heal and a soft bone-callous forms at the site of the osteotomy (latency). In an adult patient, this takes approximately one week, in a child it could take two to five days.

In the next phase of distraction osteogenesis, the distractor is activated—periodically—to separate the bone segments, and to stretch the soft-callus (activation). Distraction is done slowly, over days or weeks, so that new bone will grow at the osteotomy, and the soft-tissues will lengthen. Typically, bone segments are moved at a rate of 1 mm per day, by activating the device multiple times a day. Distraction continues until the bone segments reach the desired alignment and the bone has been lengthened the desired amount. The callous is then allowed to mature and harden resulting in a longer intact bone (consolidation). During this last phase of the distraction osteogenesis procedure, the distractor remains in place, inactive, until the bone-callus hardens.

Distraction osteogenesis was first introduced as an option for lengthening long bones, like those of the leg. Facial surgeons adopted the long bone techniques to the facial skeleton and have since used distraction osteogenesis to lengthen and reshape the midface, maxilla, and cranium. For example, craniofacial distractors can be used to lengthen the short bones during mandibular distraction, to bring retruded bones forward (e.g., LeFort distraction), and to repair bone defects (e.g., transport and alveolar distraction). However, compared with long bone distractors, the use of craniofacial distractors includes formidable challenges. While long bone distractors separate bone fragments along a relatively simple and straight path, craniofacial distractors must separate the bone segments following complex geometrical paths that are unique for each patient. Moreover, while long bone distractors have no extraordinary size constraint, craniofacial distractors must be small enough to fit into the available anatomical space under the facial soft tissues to aid in protecting the device and treatment site from external trauma and without interfering with activities of daily life (e.g., dressing, eating, talking). Craniofacial distractors must also be small enough to avoid organ tissue damage (e.g., TMJ, nerves, teeth) while also maintaining the sterility of the wound. Adding to the challenges of size constraint, craniofacial distractors are often smaller than the gap they are used to create.

Historically, most craniofacial distractors are rectilinear. That is, they can only move bone segments in a straight line. Unfortunately, rectilinear devices rarely produce good outcomes. Craniofacial deformities warp the bones of the head into complex shapes that cannot be corrected without three-dimensional movements. To overcome this limitation, inventors have designed adjustable devices that allow course changes during device activation. Unfortunately, the adjustments are limited and the devices are difficult to use.

Even if fully adjustable devices were available they can be impractical, for several reasons. Fully adjustable devices tend to be very complicated and are difficult to miniaturize to a scale appropriate to the confines of the head. Even if an appropriate fully-adjustable device can be made the correct scale, use of such devices would be burdensome and impractical requiring the operating surgeon to adjust six different knobs during distraction. Moreover, experience with simpler adjustable devices shows that making mid-course adjustments is non-intuitive and fallible.

Accordingly, there is a need in the art for a small, nonadjustable, craniofacial distractor that can move bone segments along a complex geometrical path that is customized/optimized for individual patients.

SUMMARY OF THE INVENTION

The present disclosure is directed to a craniofacial distractor for craniofacial surgery and a method and system for designing the same. The apparatus may include an orthopedic distraction device comprising a steering apparatus, an anchoring member and a distraction drive mechanism. The steering apparatus directs movement of the device along a helical-shaped distraction path and may include an outer sleeve and a telescoping inner member. The anchoring member couples the steering apparatus to a first and second bone segment of a patient. The distraction drive mechanism drives movement of the steering apparatus along the distraction path, where the steering apparatus is movable along the helical-shaped distraction path to create gap between the first and second bone segments. The distraction drive mechanism may include at least one of a worm-rack drive, flexible wires, friction-ratchet mechanism, and a hydraulic mechanism. When the distraction drive mechanism comprises a worm-rack drive, the worm-rack drive may include a worm gear rotatably coupled to the outer sleeve where the worm gear is threadably coupled to a toothed surface provided on the inner member, such that rotation of the worm gear causes the inner member to move along the distraction path. The worm-rack drive may be positioned on one of an inferior, superior, lateral, and medial surfaces of the steering apparatus. An activation port of the distraction mechanism may be coupled to the worm gear, where the activation port receives rotational input forces that drive rotation of the worm gear. An extension arm may be coupled to the activation port such that rotation of the extension arm provides an input rotation to the distraction mechanism and results in a corresponding driving movement of the steering apparatus along the distraction path. The extension arm may be sized and configured to extend through a patient's skin or oral mucosa. The extension arm may be coupled to the activation port at a universal joint-type coupling. The worm-rack drive may include an anti-rotation mechanism for limiting rotational movement of the worm gear. The anti-rotation mechanism may include a locking member coupled to an end of the worm gear at a position along a longitudinal axis of the worm gear and an engaging member coupled to the outer sleeve such that engagement between the locking member and the engaging member resists rotational movement of the worm gear. The engaging member may comprise a compliant material that limits rotational movement of the locking member, where the compliant material allows rotational movement of the locking member provided at a rotational force below a threshold resistive force of the engaging member. The engaging member may comprise a bow spring and the locking member may have a non-circular shape in cross-section.

The distraction drive mechanism may also comprise a flexible screw extending within the inner member and rotatably coupled to the outer sleeve. The flexible screw may be threadably coupled to the inner member and also rotate freely with respect to the outer sleeve, such that rotation of the flexible screw causes the inner member to translate along the outer sleeve. The inner member may include a threaded opening at its proximal end that engages the threads of the flexible screw, accordingly rotation of the flexible screw causes the inner member to translate along the outer sleeve. The flexible screw may include a shoulder at its proximal end for rotatably engaging an opening at a proximal end of the outer sleeve. The distraction drive mechanism may also include an activation port coupled to the proximal end of the flexible screw, the activation port may extend from the proximal end of the outer sleeve and receives rotational input forces to drive rotation of the flexible screw. An extension arm may be coupled to the activation port where rotation of the extension arm provides an input rotation that results in a corresponding driving movement flexible screw. The extension arm may be sized and configured to extend through a patient's skin or oral mucosa. The extension arm may be coupled to the activation port at a universal joint-type coupling.

The inner member of the steering apparatus may extend from a distal opening provided on the outer sleeve. Movement of the inner member and outer sleeve along the helical-shaped distraction path causes the inner member to further extend from the distal opening of the outer sleeve. The steering apparatus may further include an intermediate sleeve extending between the outer sleeve and the inner member, where the intermediate sleeve extends from a distal opening provided in the outer sleeve and the inner member extends from a distal opening provided in the intermediate sleeve. Movement of the steering apparatus along the distraction path will cause the intermediate sleeve to further extend from the distal opening of the outer sleeve and the inner member to further extend from the distal opening of the intermediate sleeve. The outer sleeve and the inner member may define a generally rectilinear cross-sectional shape. The outer sleeve and the inner member may also define a generally circular cross-sectional shape.

The anchoring member of the distraction device may include a first footplate for coupling the outer sleeve to the first bone segment and a second footplate for coupling the inner member to the second bone segment. The first and second footplates may be sized and shaped to correspond to a surface of the first and second bone segments, respectively. Each of the first and second footplates may also include an opening for receiving a bone screw to fix the first and second footplates to the first and second bone segments, respectively, where the location of each of the openings is predetermined to lay over a portion of the first and second bone segments having an increased thickness and avoiding a blood vessel, nerve, and tooth.

With respect to the present distraction device, at least one of the outer sleeve and inner member may be movable along the distraction path between a first position of the first and second bone segments and a second position of the first and second bone segments. The second position of the first and second bone segments may identify a predetermined re-aligned position of the first and second bone segments. The helical-shaped distraction path is the simplest path that will place the bone segments in the second (final) position. In the particular case of mandibular distraction, the helical-shaped distraction may be defined as the path of movement that minimizes condylar displacement/loading between the first and second bone segments during device activation, while realigning the bone segments into ideal position.

In another aspect, the present disclosure is directed to a distraction device comprising a steering apparatus including a carriage member coupled to a rail member, an anchoring member and a distraction drive mechanism. The carriage member may be slidingly coupled to a rail member, where movement of the carriage member with respect to the rail member is along a distraction path of the device. The rail member may include a groove defining the distraction path. The anchoring member couples the steering apparatus to a first and second bone segment. The distraction drive mechanism drives movement of the rail member along the distraction path, where the rail member moves along the distraction path to create a gap between first and second bone segments. The distraction drive mechanism may include a flexible screw extending within a central opening of the rail member, where the flexible screw engages a threaded opening provided in the carriage member such that rotational movement of the flexible screw causes a corresponding movement of the carriage along the distraction path. When the distraction drive mechanism comprises a flexible screw, the screw may be retained within and rotates freely with respect to the rail member and also threadably engage a threaded opening provided in the carriage member such that rotation of the flexible screw causes the carriage member to move along and within the rail member along the distraction path. An activation port of the distraction drive mechanism may be provided at a distal end of the rail member, the activation port for receiving rotational input forces to drive rotation of the flexible screw. The anchoring member may include a first footplate for coupling the rail member to the first bone segment and a second footplate for coupling the carriage member to the second bone segment. The first and second footplates may be sized and shaped to correspond to a surface of the first and second bone segments, respectively. Each of the first and second footplates may also include an opening for receiving a bone screw to fix the footplate to the first and second bone segments, respectively, where the location of each of the openings is predetermined to lay over a portion of the first and second bone segment having an increased thickness and avoiding a blood vessel, nerve, and tooth.

In another aspect, the present disclosure is directed to a steering apparatus including a first and second carriage member and a rail member, an anchoring member and a distraction drive mechanism. Each of the first and second carriage members are slidingly coupled to the rail member, where movement of the first and second carriage members with respect to the rail member is along a distraction path of the device. The rail member may include a groove defining the distraction path. The anchoring member couples the first and second carriage members to a first and second bone segment, respectively. The distraction drive mechanism drives movement of the steering apparatus along the distraction path, where the movement of the first and second carriage member along the distraction path creates a gap between first and second bone segments. The rail member may direct movement of the first and second carriage members along an entire distraction distance. Each of the first and second carriage members may include a footplate for coupling to the first and second bone segments, respectively, where the footplates are sized and shaped to correspond to a surface of the first and second bone segments, respectively. The location of each of the openings may be predetermined to lay over a portion of the first and second bone segment having an increased thickness and avoiding a blood vessel, nerve, and tooth.

The distraction drive mechanism may also include a flexible screw extending within a central opening of the rail member, where the flexible screw retained within and rotates freely with respect to the rail member. A first portion of the flexible screw may include a thread having a clockwise orientation and a second portion of the flexible screw may include a thread having a counterclockwise orientation, wherein the first portion of the screw engages a corresponding threaded opening provided in the first carriage member, and the second portion of the screw engages a corresponding threaded opening provided in the second carriage member. The first and second carriage members may be movable along the rail member from an initial position where the carriage members are positioned intermediate a proximal and distal end of the rail member. Rotation of the flexible screw may drive movement of the first and second carriage members from the initial position towards opposing ends of the rail member, such that the first carriage member moves in a direction generally towards a proximal end of the rail member and the second carriage member moves in a direction generally towards a distal end of the rail member. An activation port of the distraction drive mechanism may be provided at one of the proximal and distal ends of the rail member.

In another aspect, the present disclosure is directed to system and method for constructing a custom craniofacial distraction device. A first step comprises, receiving an initial patient model comprising a three-dimensional rendering of a patient's skull, and presenting the initial patient model at a control interface for receiving user input to a user via a graphical user interface. Receiving a three-dimensional rendering of the patient may include receiving at least one of a CT image of a patient's head and a three-dimensional images of the patient's teeth, and using at least one of the CT image and the dental image to create the initial patient model. The CT image and the dental image may be merged to create the initial patient model including a patient's skull, teeth, nerves, and soft-tissues.

A next step may include, receiving an input corresponding to a user's interaction with the control interface identifying a cut site on the initial patent model for separating the model into a first and second bone segment, where either one of the bone segments is movable. A next step may include, receiving an input corresponding to a user's interaction with the control interface identifying an initial position of the first bone segment (e.g., identifying the initial position of a marker array associated with the first bone segment, the marker array including a number of three-dimensional points associated with the first bone segment and their corresponding three-dimensional position/location data) and an initial position of the second bone segment (e.g., identifying the initial position of a marker array associated with the second bone segment, the marker array including a number of three-dimensional points associated with the second bone segment and their corresponding three-dimensional position/location data). A next step may include, receiving an input corresponding to a user's interaction with the control interface identifying an adjusted three-dimensional position the bone segments (e.g., position/location data associated with the (adjusted) location of the points of the first and second bone segment marker arrays). A next step may include, determining a helical-shaped distraction path between the initial position and the adjusted three-dimensional position. A next step may include, presenting an adjusted patient model comprising a three-dimensional rendering of a patient's skull with the bone segments in the adjusted three-dimensional position. A next step may include, comparing the initial position of the first and second bone segments (e.g., the initial position/location data of the corresponding marker arrays) with an adjusted position of the first and second bone segments (e.g., the adjusted position/location data of the corresponding marker arrays) to determine a helical-shaped distraction path therebetween. A next step may include constructing a distraction apparatus based on the determined helical-shaped distraction path.

The system and method for constructing a custom craniofacial distraction device may further include the step of receiving an input corresponding to a user's interaction with the control interface identifying a second cut site on the initial patent model for separating the model to include a third segment, the third bone segment movable with respect to the second bone segment. A next step may include, receiving an input corresponding to a user's interaction with the control interface identifying an initial position of a third bone segment (e.g., identifying the initial position of a marker array associated with the third bone segment, the marker array including a number of three-dimensional points associated with the third bone segment and their corresponding three-dimensional position/location data). A next step may include, receiving an input corresponding to a user's interaction with the control interface identifying an adjusted three-dimensional position of the third bone segment (e.g., position/location data associated with the (adjusted) location of the points of the third bone segment marker array). A next step may include, presenting an adjusted patient model comprising a three-dimensional rendering of a patient's skull with the second and third bone segments in their adjusted three-dimensional position. A next step may include, comparing the initial position of the first and third bone segments (e.g., the initial position/location data of the corresponding marker arrays) with an adjusted position of the first and third bone segments (e.g., the adjusted position/location data of the corresponding marker arrays) to determine a helical-shaped distraction path therebetween. A next step may include, constructing a second distraction apparatus based on the determined helical-shaped distraction path between the first and third bone segments. A next step may include, presenting an animation of the movement between the first and second bone segments along the distraction path, and presenting an animation of the movement between the first and third bone segments along the distraction path.

Presenting the adjusted patient model may further include identifying any interference points between the first and second bone segments and calculating an interference volume corresponding to the identified interference points. Presenting the adjusted patient model may further include identifying any interference points between the first, second, and third bone segments and calculating an interference volume corresponding to the identified interference points.

With respect to the system and method for constructing a custom craniofacial distraction device capable of movement along a helical-shaped distraction path, the constructed distraction device may comprise, for example, a telescoping-type distraction device including, for example, a sleeve and telescoping member, where movement of the telescoping member is along the determined helical-shaped distraction path. The constructed distraction device may also comprise a rail and carriage-type distraction device including, for example, a carriage member slidingly coupled to a rail member, where movement of the carriage member with respect to the rail member is along the determined helical-shaped distraction path. The constructed distraction device may also comprise a rail and carriage-type distraction device including two carriage members slidingly coupled to the rail member, where movement of the two carriage members with respect to the rail member is along the determined helical-shaped distraction path.

Constructing the distraction apparatus may further comprise receiving an input corresponding to a user's interaction with the control interface identifying dimensional parameters of the distraction device including at least one of cross-sectional dimensions and shape of the rail member, length of the rail member, a cross-sectional dimension and shape of the carriage member, and a starting position of the carriage member along the determined helical-shaped distraction path. The identified length of the rail member may be equal to or greater than a length of the determined helical-shaped distraction path. Receiving an input corresponding to a user's interaction with the control interface may include identifying a location on the initial patient model for positioning of the distraction apparatus. Identifying the location for positioning the distraction apparatus may include identifying an offset from a bone surface on the initial patient model. Where the distraction apparatus is a rail and carriage-type distraction device, constructing the distraction apparatus further comprises creating a model of the rail member (or sleeve when distraction apparatus is a telescoping-type distraction device) by locating a two-dimensional cross-section of the rail member at an origin of the determined helical-shaped distraction path such that the cross-section is aligned orthogonally with the path, lengthening the determined helical-shaped distraction path corresponding to the length of the rail member, and creating a three-dimensional model of the rail member by extending the two-dimensional cross-section of the rail member along a length of the helical-shaped distraction path. Constructing the distraction apparatus may further comprises creating a model of the carriage member (or telescoping member when the distraction apparatus is a telescoping-type distraction device) by aligning a two-dimensional cross-section of the carriage member at an origin of the determined helical-shaped distraction path such that the cross-section is aligned orthogonally with the path, locating the two-dimensional cross-section of the carriage member at the starting position of the carriage member along the determined helical-shaped distraction path, and creating a three-dimensional model of the carriage member by extending the two-dimensional cross-section of the carriage member along a length of the helical-shaped distraction path. Constructing the distraction apparatus further comprises manufacturing a rail member and a carriage member corresponding to the created models by 3D printing, or milling The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

The invention is explained in even greater detail in the following drawings. The drawings are merely examples to illustrate the structure of preferred devices and certain features that may be used singularly or in combination with other features. The invention should not be limited to the examples shown. In the drawings, like reference numbers and designations in the various drawings indicate like elements.

FIG. 1 is an anatomical model including an example distraction device where the patient's anatomy is illustrated in an initial alignment;

FIG. 2 is an anatomical model including an example distraction device where the patient's anatomy is illustrated in an intermediate alignment;

FIG. 3 is an anatomical model including an example distraction device where the patient's anatomy is illustrated in a final/desired alignment;

FIG. 6 is a schematic representation of the handedness of helical movement of a rigid body about an axis (left-handed, right-handed);

FIG. 35 is a portion of an example graphical user interface;

Figure 4:
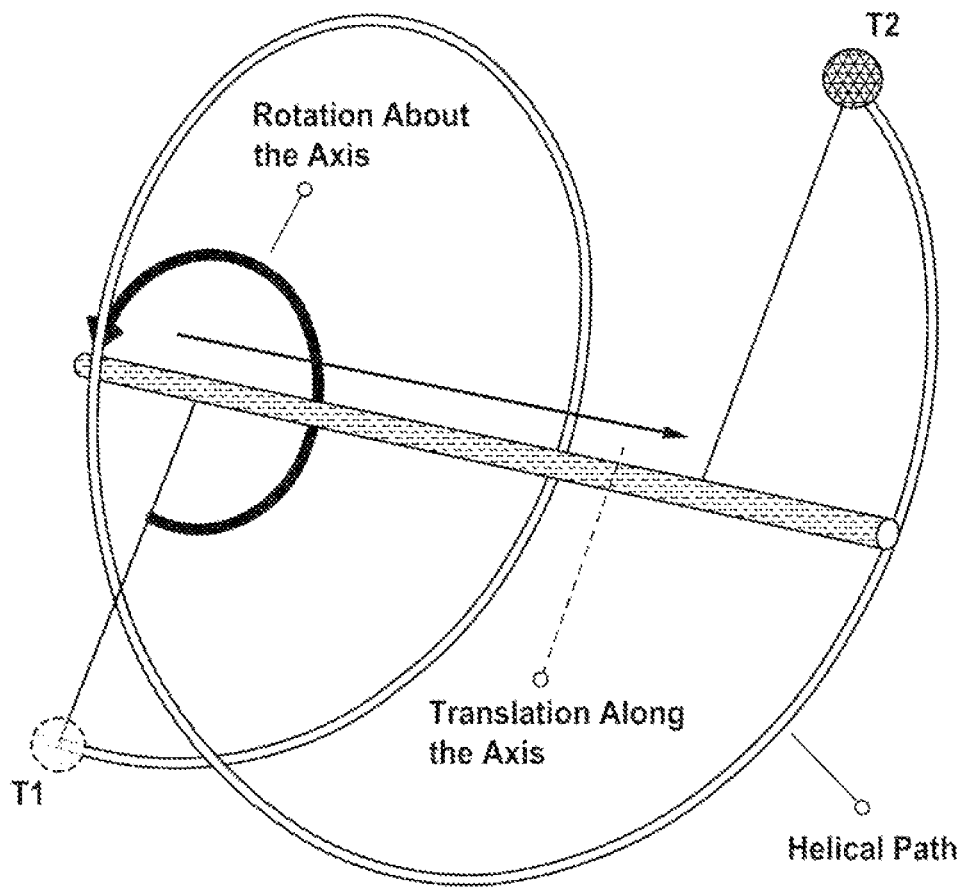
FIG. 4 is a schematic representation of helical movement of a rigid body about an axis.

Certain examples of the invention will now be described with reference to the drawings. In general, such embodiments relate to a craniofacial distractor that can move bone segments along a complex geometrical path.

DESCRIPTION OF THE PREFERRED EMBODIMENTS

The present invention may be understood more readily by reference to the following detailed description of preferred embodiments of the invention and the Examples included therein and to the Figures and their previous and following description.

The present disclosure is directed to a craniofacial distractor that can move bone segments along a complex geometrical path that is customized and optimized for individual patients. The present distractor contemplates a non-adjustable device designed with a distraction path optimized for each patient, such that the distractor would only require activation. For each patient, an optimal distraction path is calculated, prior to surgery, and a custom device made. Though described in the context of use on a patient's face and cranium, it is contemplated that the present distractor can be used on any part of a patient's anatomy including, for example, the bones of the leg, arm, or torso.

Distraction devices must perform two distinct functions: fixation and distraction. Fixation prevents the movement of the bone segments at each interval of the distraction procedure. Distraction separates the bone segments to elongate a bone or to change its position. For new bone to form at the site of the bone cut, the only movement the segments should have is the tiny separation that occurs when the device is activated. Instability of the distractor between bone segments could misdirect the relative movement between the bone segments, thwart osteogenesis, and cause non-union. As will be described in more detail below, the present distractor device is capable of rigidly stabilizing the bone segments.

Distraction devices must also be designed and positioned with respect to the patient's anatomy to prevent organ or tissue damage. A complication of mandibular distraction is TMJ ankyloses, the fusion of a jaw joint. This severe complication results from abnormal TMJ loading. Any distractor that torques, or misplaces, the mandibular condyles can cause ankyloses. Mandibular condylar displacement, or torqueing, occurs during device activation when the component that steers the distractor movement is not optimally shaped. As will be described in more detail below, the present disclosure utilizes custom mandibular distractors that avoid unwanted condylar movements by providing a helical distraction path of motion that avoids condylar displacement at any distraction interval. Another way of avoiding injury is to use distractor footplates (and arms) customized to the particular patient's anatomy. Custom footplates can have plate-holes that are optimally positioned over strong bone and away from vessels, nerves, and teeth.

As will be described in more detail below, the present disclosure utilizes footplates customized to avoid a patient's sensitive anatomy.

Distraction devices must also be designed to fit into the available anatomical space. In a distraction operation, surgeons lift the soft-tissue to expose the skeleton near the planned bone cut. When the periosteum is lifted, a small pocket forms between the bone and the non-stretchy periosteum. It is in this pocket where the distractor is placed. There is generally an inverse relationship between the length of a distractor and the space available for it. Small bones need long distractors because, to correct a severe deformity, the bone segments must move extended distances. In small bones, however, the space available to accommodate the devices is minimal. As will be described in more detail below, the present disclosure provides an extendable/telescoping distraction device with a helical distraction path of a size and structure suitable to fit into the limited anatomical space of the facial skeleton.

Distraction devices must also be designed to maintain the sterility of the wound/treatment site. As described above, craniofacial distractors are implanted in a small pocket formed between the patient's bone and the adjacent soft-tissue. The distractor is activated via an extension arm that exits the body through the skin or oral mucosa. As result, the part of activating arm that is outside the body is colonized with bacteria. Using traditional devices there is risk of infection during activation as the contaminated portion of the activating arm is brought into contact with/through the wound. To prevent this, the present craniofacial distractor includes an activation port/extension arm position to prevent the movement of the arm through the wound.

In sum, and as will be described in more detail below, the present craniofacial distractor carries the bone segments into an ideal alignment, stabilizes the bone segments, prevents organ/tissue damage, fits in the available anatomical space, maintains sterility of the wound, can be activated from different directions, is comfortable, is easily installed and easily removed, is protected from external trauma, and remains hidden during use. It is also contemplated that the present craniofacial distractor can be used in any craniofacial area (i.e., mandible, maxilla, midface, and cranium), and for each application (conventional and transport distraction).

FIGS. 1-3 illustrate an example distractor used to move various bones/bone segments of the patients face along a geometrically complex distraction path. FIG. 1 provides the initial position of the patient's facial anatomy. The distraction device can move the various bones/bone segments (e g, mandible bone segments) from an initial position, along the distraction path via any number of intermediate positions/alignment (FIG. 2), where the mandible bone segment is brought forward into a final/desired alignment (FIG. 3). As will be described in more detail below, movement along the distraction path involves moving the moving bone segment(s) through an array of three-dimensional rotations and translations before they reach the desired alignment.

The free movement of a rigid-body in three-dimensional space is called general motion. A body undergoing general motion can reach an alignment by following numerous different paths. This movement, however, can be simplified as a combination of rotation around a unique axis and translation along the same axis, i.e., helical motion (FIG. 4). Thus, any general motion of a rigid-body can be streamlined to a helical path. It is therefore contemplated that a distractor having a distraction path shaped like a helix can used to move bone segment(s) into any new (three-dimensional) location and orientation with respect to the starting orientation and adjacent facial structure. As will be described below with respect to the present distraction device, each patient/transformation will require a unique distraction path defined by a helix with a unique shape and orientation.

Figure 5:
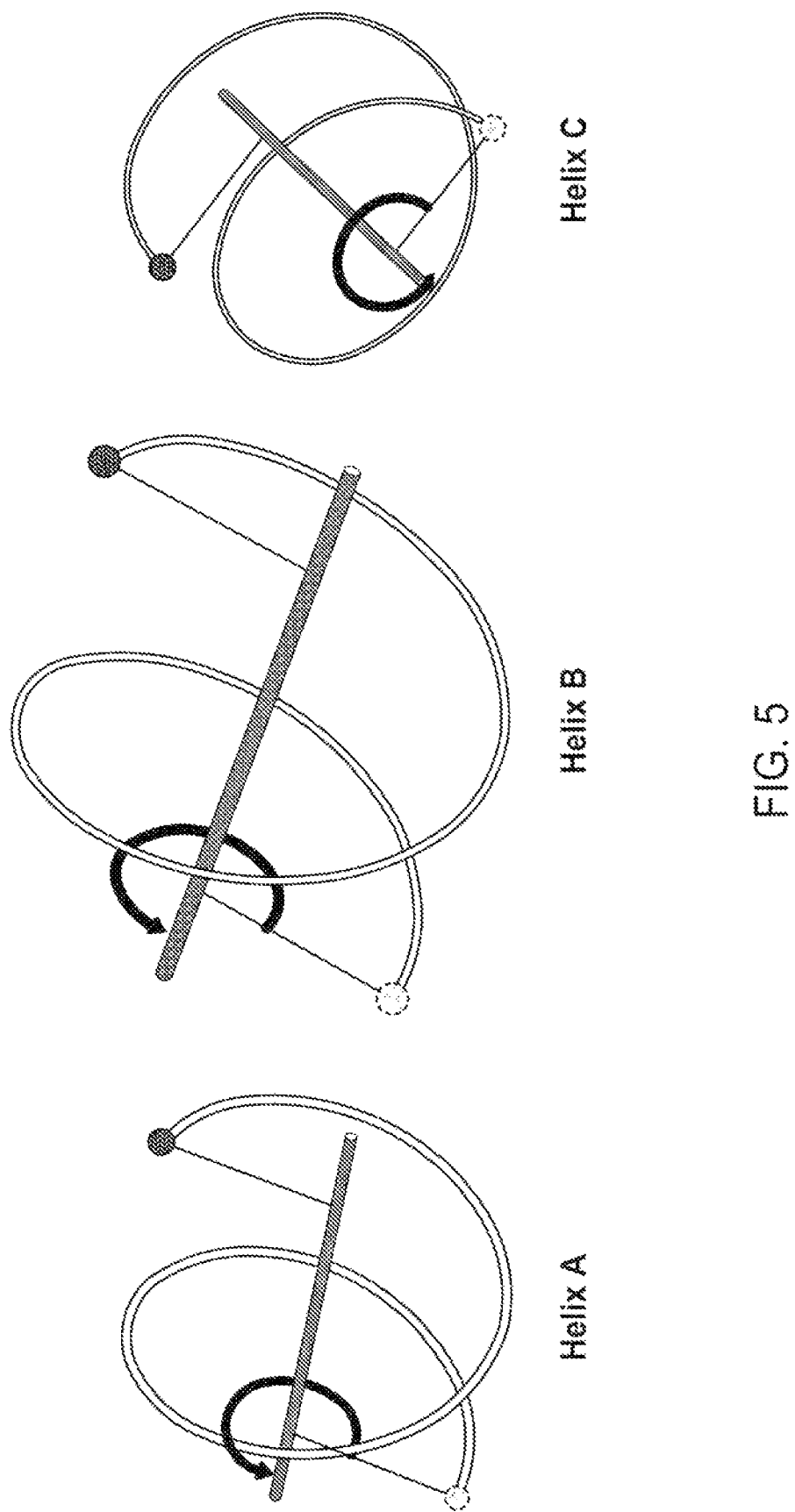
FIG. 5 is a schematic representation of helical movement of a rigid body about an axis illustrating various positions and orientations of the axis.
Figure 7:
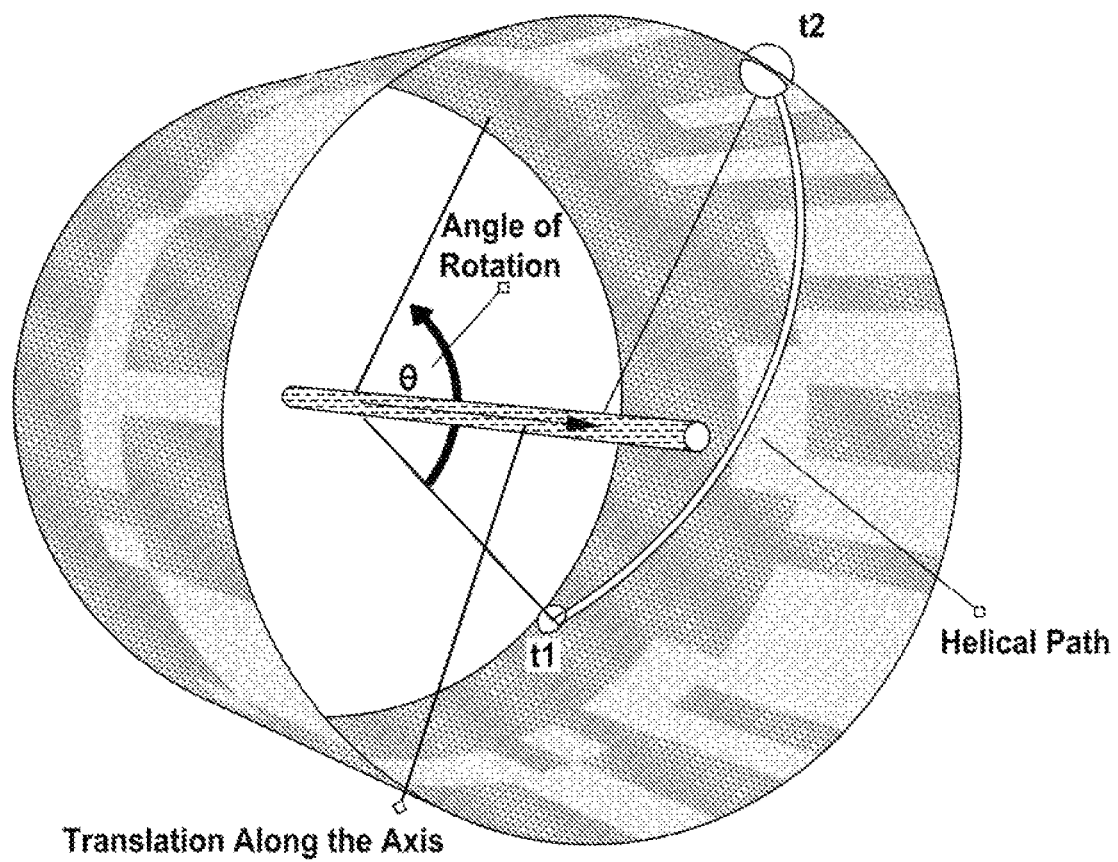
FIG. 7 is a schematic representation of helical movement of a rigid body about an axis.

Helical paths may be defined with respect to the position and orientation of the helical axis in three-dimensional space. For example, identical helical paths (A, B, C) can have axes with various positions and orientations in three-dimensional space (FIG. 5). A helical path may also be defined with respect to the handedness of the movement around the axis, i.e., left-handed, right-handed (FIG. 6). A helical path may also be defined with respect to the angle of rotation ($\theta$) about the axis of the helix and by the amount of translation along the axis (FIG. 7).

FIG. 8A is a perspective view of an example orthopedic craniofacial distractor 100 illustrated on an anatomical model of a patient's skull with the patient's anatomy in an initial alignment and FIG. 8B is a perspective view with the patient's anatomy in a final/desired alignment. The distractor 100 comprises a steering apparatus that directs movement of the distractor 100 along a helical-shaped distraction path. The steering apparatus includes an outer sleeve 110 and a telescoping inner member 112 that extends from/through an opening provided in the end of the outer sleeve 110. Movement of the inner member 112 and outer sleeve 110 along the helical-shaped distraction path causes the inner member 112 to further extend from the distal opening of the outer sleeve 110. As illustrated in FIGS. 8A and 8B, Axis A identifies the axis of rotation of the helical-shaped distraction path, arrow B identifies the direction of angular displacement of the helical-shaped distraction path, and arrow C identifies the direction of linear displacement.

Figure 8:
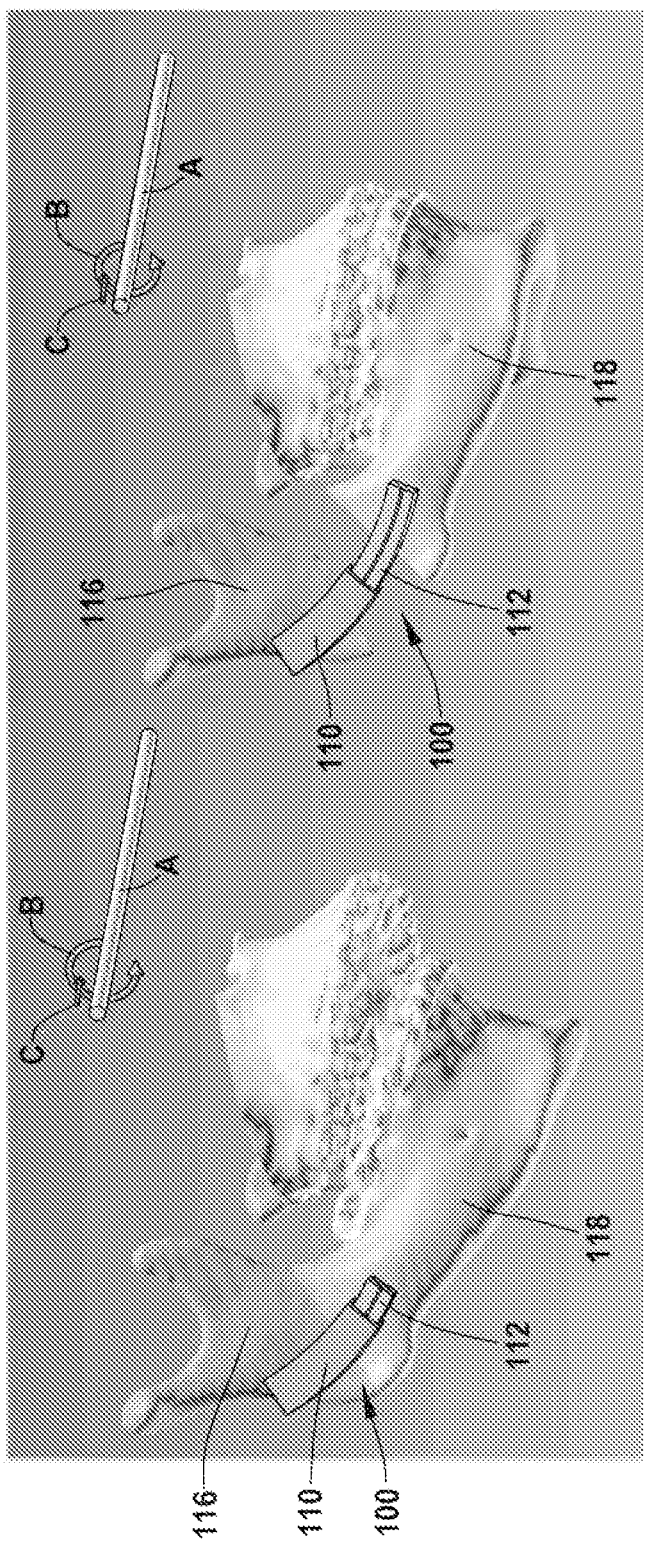
FIG. 8A is a perspective view of an anatomical model including an example distraction device where the patient's anatomy is illustrated in an initial alignment.
FIG. 8B is a perspective view of an anatomical model including an example distraction device where the patient's anatomy is illustrated in a final/desired alignment.
Figure 9:
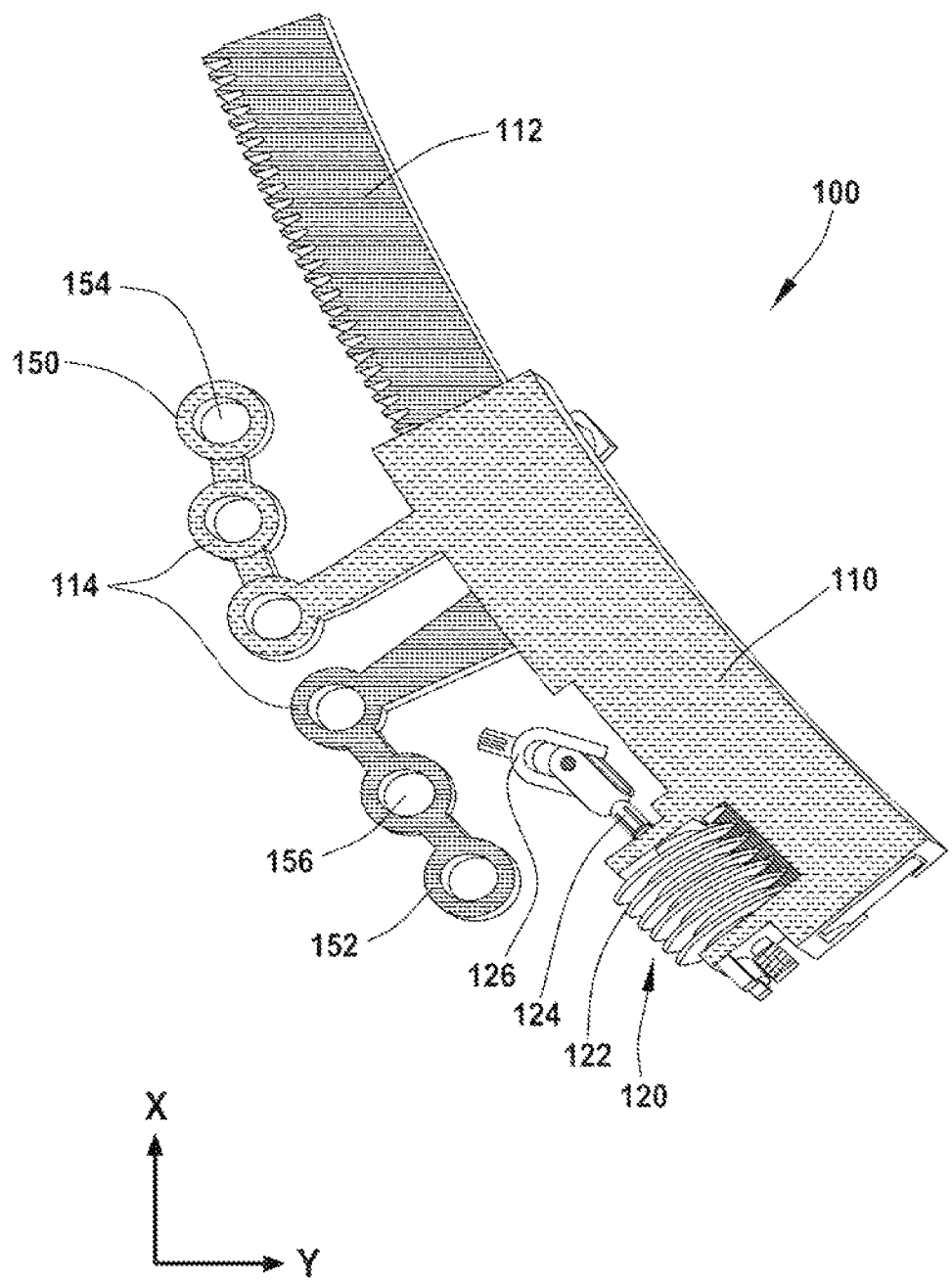
FIG. 9 is a side perspective view of the distraction device of FIG. 8 utilizing a worm-rack style of driving mechanism.

FIG. 9 provides a perspective of the distractor 100 of FIG. 8, including anchoring members 114 used to couple the distractor 100 to adjacent bone segments 116, 118. In this example the first and second bone segments 116, 118 include adjacent portions of the mandible. The distractor 100 of FIG. 9 also includes a driving mechanism 120 that drives movement of the steering apparatus (i.e., outer sleeve 110 and inner member 112) along the distraction path. The outer sleeve 110 and inner member 112 are movable along the helical-shaped distraction path to create gap and alignment between the first and second bone segments 116, 118. The drive mechanism 120 can include various components for directing movement between the outer sleeve 110 and inner member 112 including, for example, a worm-rack drive, flexible wires, friction-ratchet mechanism and a hydraulic drive mechanism.

Figure 10:
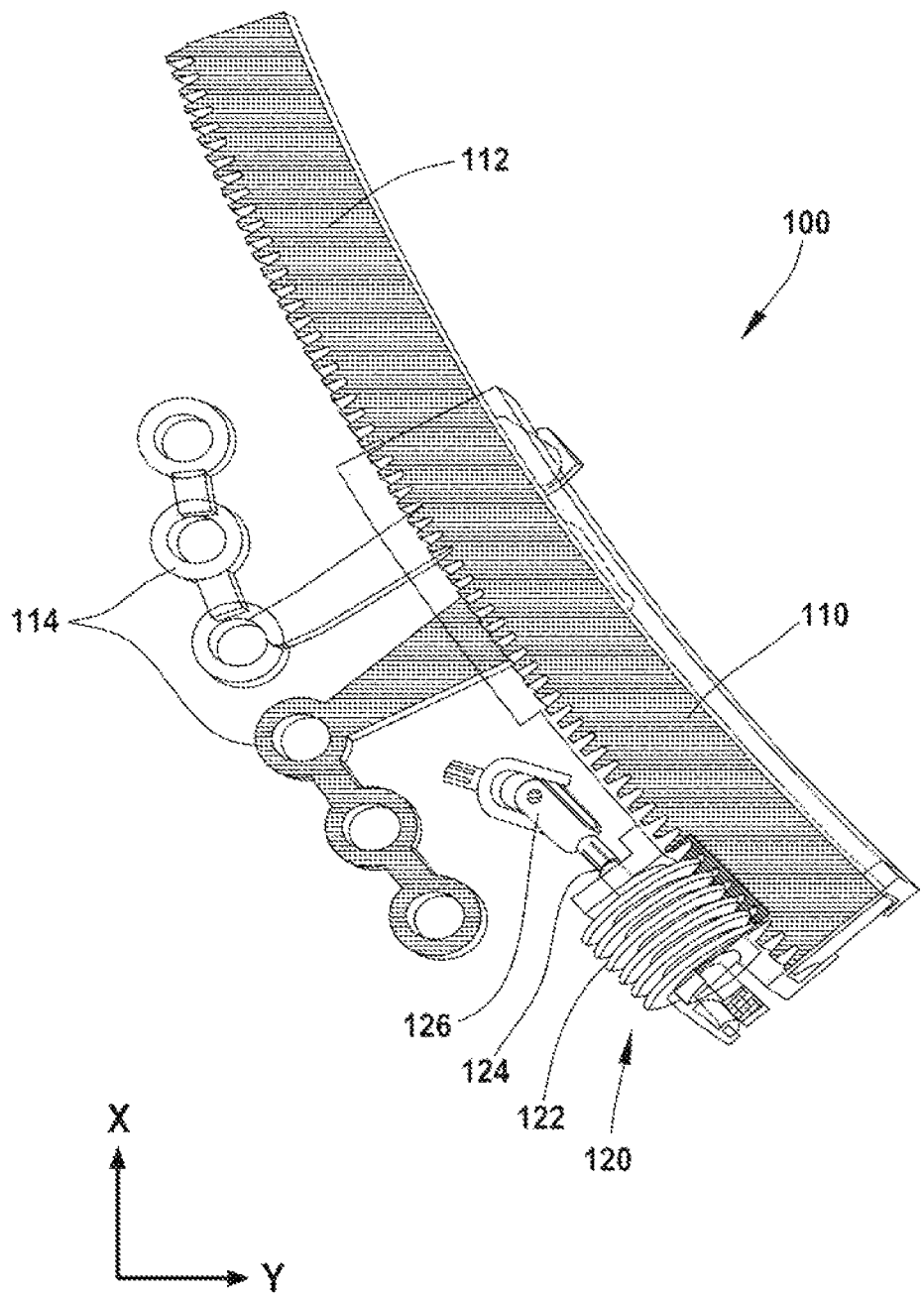
FIG. 10 is side perspective of the distraction device of FIG. 9 with the outer sleeve illustrated as transparent.
Figure 11:
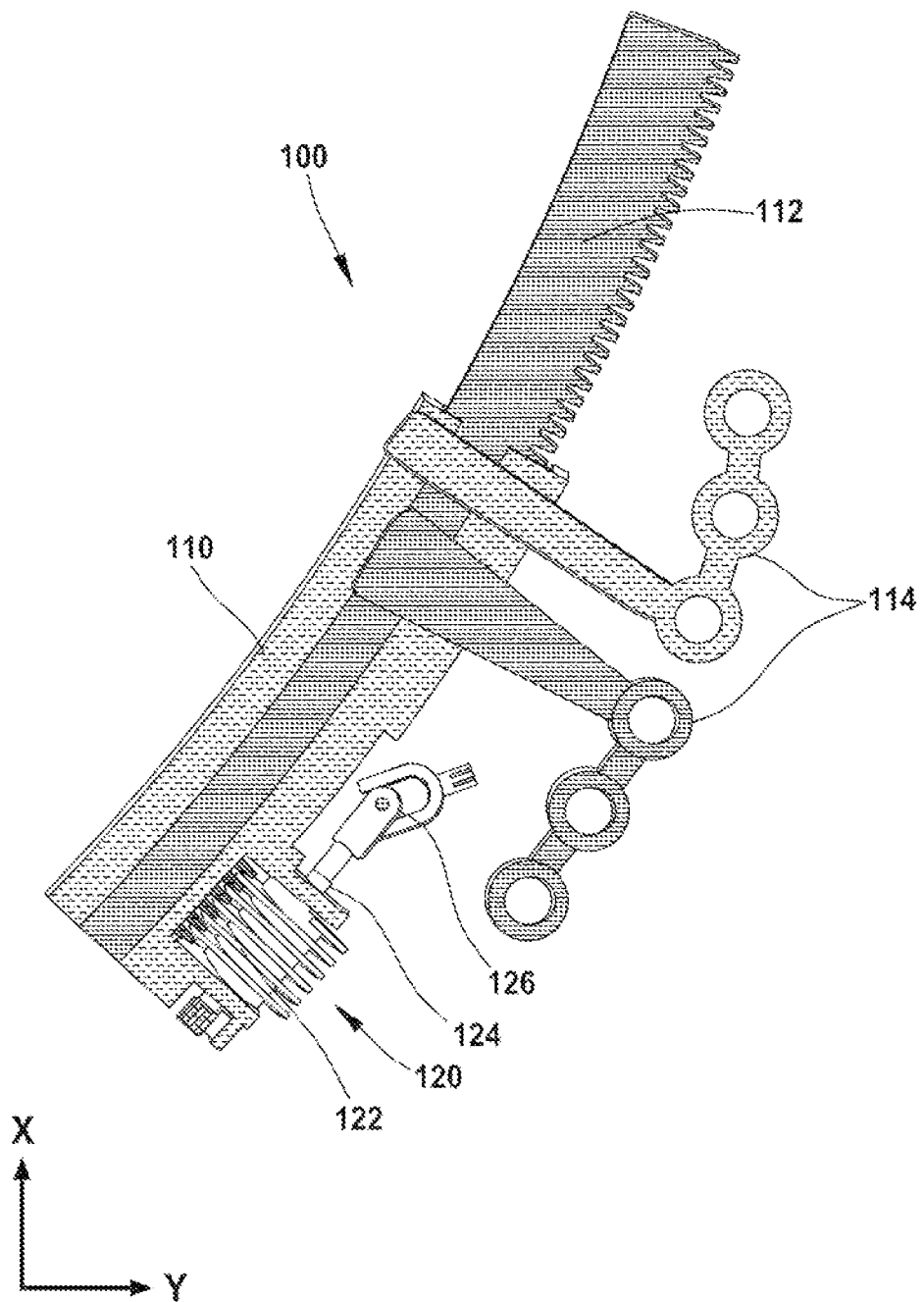
FIG. 11 is a side perspective of the distraction device of FIG. 9.
Figure 12:
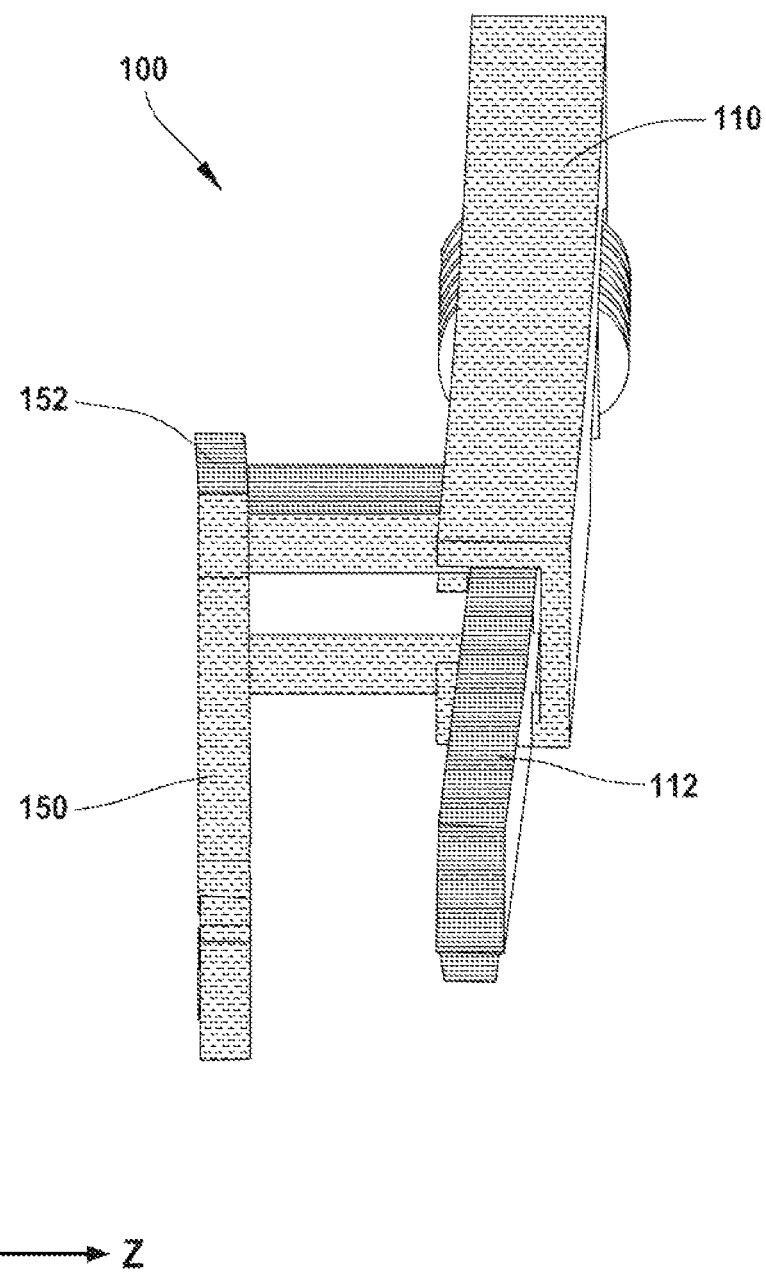
FIG. 12 is a top perspective view of the distractor of FIG. 9.
Figure 14:
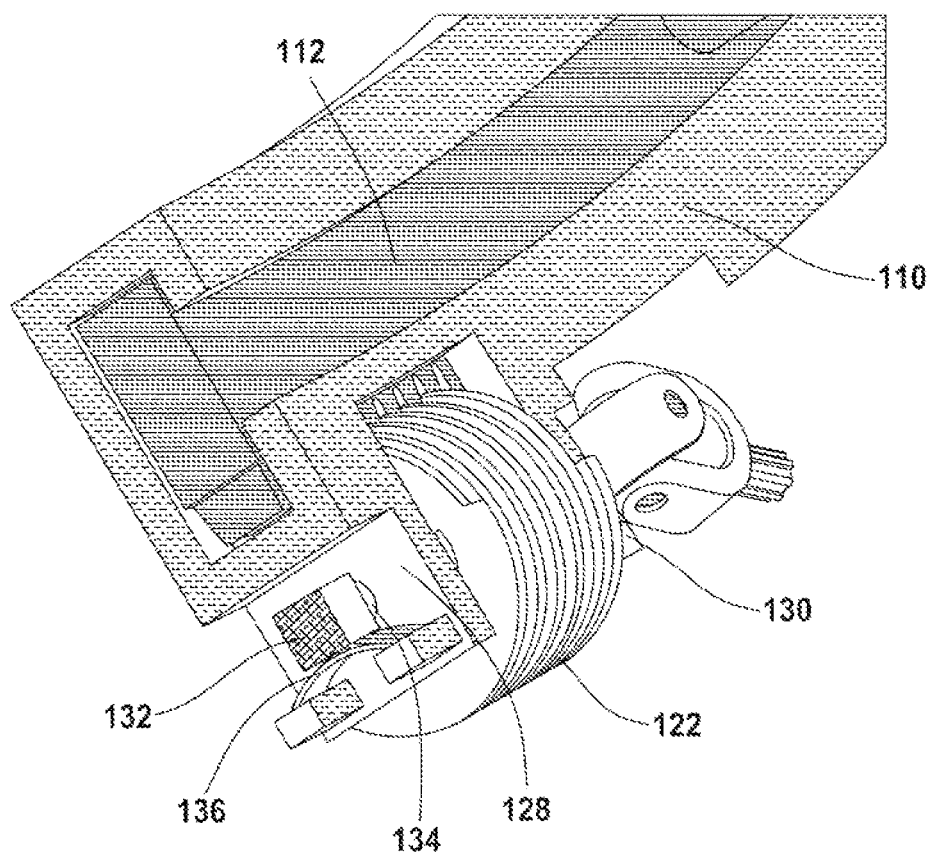
FIG. 14 is a partial end perspective view of the distractor of FIG. 9.

FIG. 9 illustrates the distractor of FIG. 8 including a worm-rack style of driving mechanism 120. FIG. 10 is perspective view of the worm-rack drive mechanism of FIG. 9 with the outer sleeve 110 illustrated as transparent. FIG. 11 is an opposite side view of the distractor 100 of FIG. 9 and FIG. 12 is top view of the distractor 100 of FIG. 9. And FIG. 14 provides a partial end perspective view of the distractor of FIG. 9.

As provided in FIGS. 9-12, 14 the worm-rack style drive mechanism 120 includes a worm gear 122 rotatably coupled to the outer sleeve 110, the worm gear 122 threadably coupled to a toothed surface provided on the inner member 112, wherein rotation of the worm gear 122 causes the inner member 112 to move along the distraction path. As illustrated in FIG. 9, the worm gear 122 is rotatably coupled to the outer sleeve 110 and includes an outer thread that engages with corresponding teeth projecting from the bottom/inferior surface of the inner member 112. Rotation of the worm gear 122 causes the thread to engage the teeth of the inner member 122 and results is a corresponding movement between the inner member 122 and outer sleeve 110. Though illustrated as positioned on the inferior surface/side of the inner member 112 and outer sleeve 110, it is also contemplated that the drive mechanism can be positioned on the superior, lateral, and/or medial surface of the steering apparatus (inner member 112 and outer sleeve 110) as required by patient anatomy, to ensure patient comfort and limit deformity caused by placement of the distractor 100.

The drive mechanism 120 can include an activation port 124 for receiving the rotational input forces that drive rotation of the worm gear 122. As provided in FIG. 9, the activation port 124 is coupled along the longitudinal axis of the worm gear 122, such that the activation port 124 is axially aligned with the rotational axis of the worm gear 122. The activation port 124 can be releasably coupled to the worm gear 122. It is also contemplated that the activation port 124 can be fixedly coupled to the worm gear 122 or integrally formed with the worm gear 122.

Figure 13A:
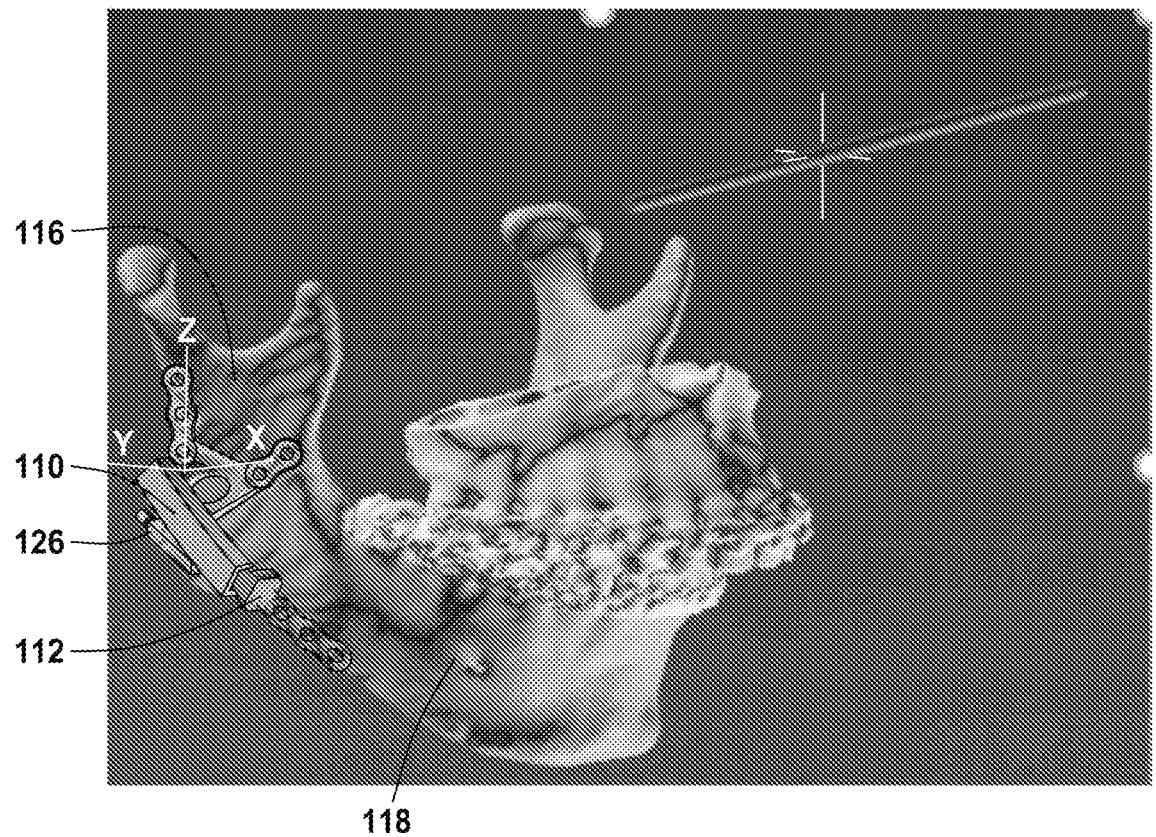
FIG. 13A is a perspective view of an anatomical model including an example distraction device where the patient's anatomy is illustrated in an initial alignment.
Figure 13B:
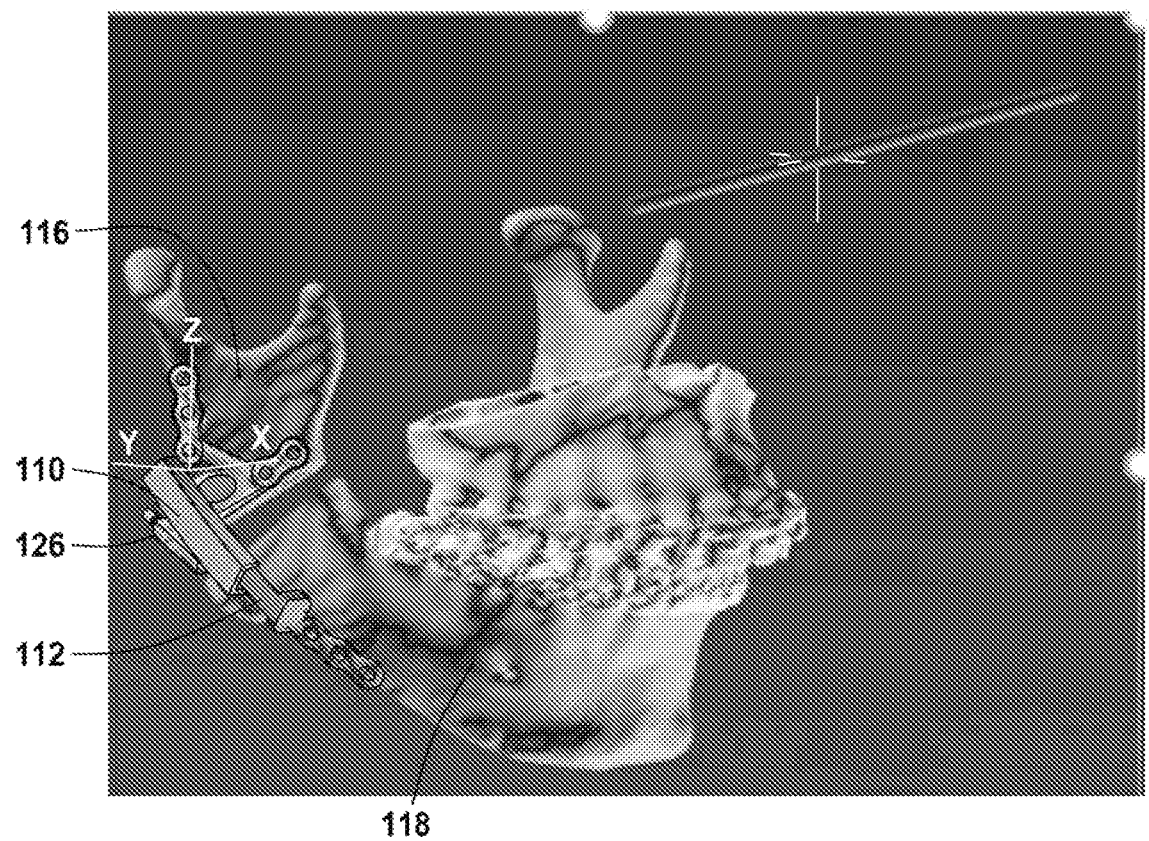
FIG. 13B is a perspective view of an anatomical model including an example distraction device where the patient's anatomy is illustrated in an intermediate alignment.
Figure 13C:
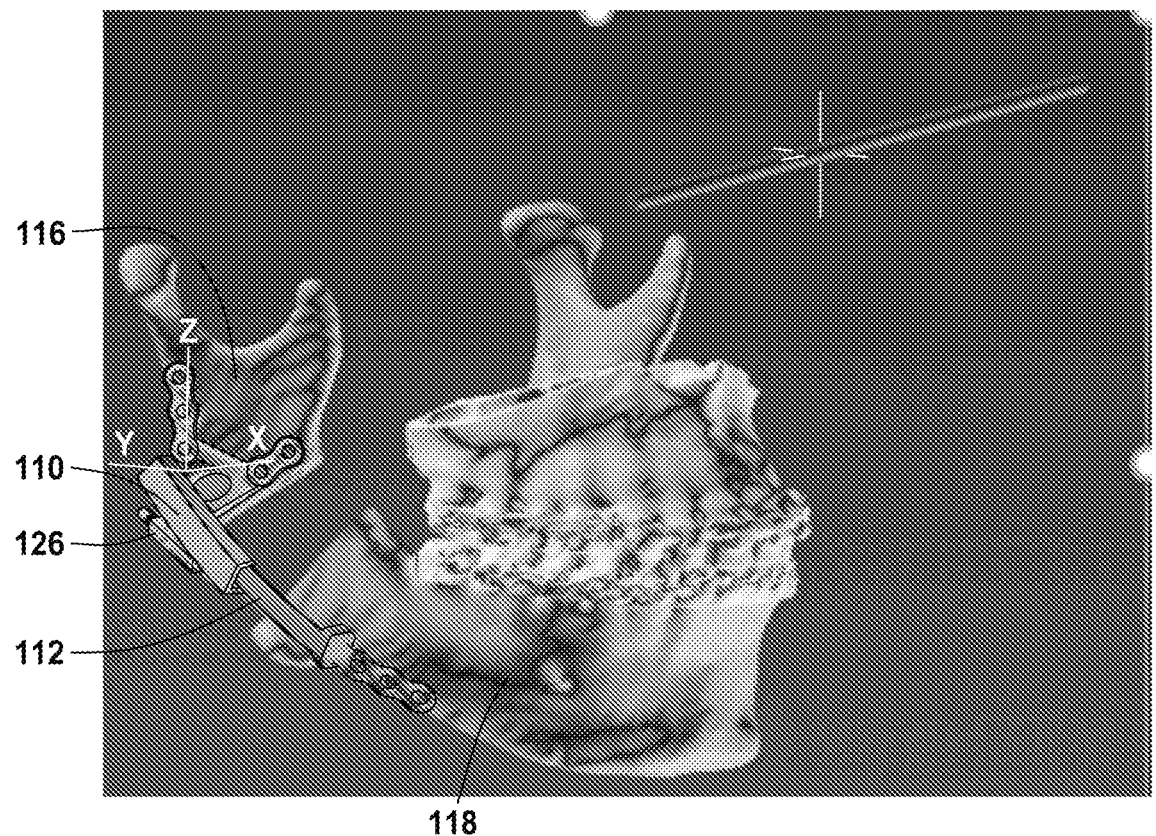
FIG. 13C is a perspective view of an anatomical model including an example distraction device where the patient's anatomy is illustrated in a final/desired alignment.

An activating/extension arm 126 is coupled to the drive mechanism 120 at the activation port 124. Rotation of the extension arm 126 provides the input rotation to the drive mechanism 120 and results in the corresponding driving movement of the inner member 112 and outer sleeve 110 along the distraction path. Specifically, the extension arm 126 is coupled to the activation port 124 and provides input rotation to the worm gear 122. Coupled to a distal end of the worm gear 122, rotation of the extension arm 126 results in a corresponding rotation of the worm gear 122. The extension arm 126 can be coupled to the activation portion 124 at a universal joint-type coupling. The extension arm 126 is sized and configured to extend from the distractor 100 and through the patient's skin or oral mucosa where it receives rotational input force from the user. To prevent bacteria on the extension arm 126 from infecting the wound, it is contemplated that the driving mechanism 120/worm gear 122 is coupled to the stationary bone segment. Because the extension arm 126 is coupled to the stationary bone segment, the extension arm 126 does not move (laterally) through the open wound in the patient's skin/oral mucosa. As illustrated in FIGS. 13A-13C, the outer sleeve 110 including activation port 126 is coupled to the stationary first bone segment 116 (upper segment of the mandible) and the inner member 112 is coupled to the mobile second bone segment 118 (lower segment of the mandible). In contrast, were the extension arm 126 coupled to the moving bone segment, driving rotation of the extension arm 126 would cause it to move through (rotationally and laterally) the open wound as the inner and outer members 112, 110 expanded along the distraction path. As a result, bacteria and other contaminates would be introduced into the wound.

It is also contemplated both the first and second bone segments 116, 118 may be mobile, in which case coupling of the inner member 112 and outer sleeve 110 to their respective bone segments may be determined based on patient anatomy and desired outcome. Though illustrated as positioned on the inferior surface/side of the inner member 112 and outer sleeve 110, it is also contemplated that the activation port 124 and extension arm 126 can be positioned on the superior, lateral, and/or medial surface of the steering apparatus (inner member 112 and outer sleeve 110) as required by patient anatomy, to ensure patient comfort and limit deformity caused by placement of the distractor 100/extension arm 126.

As described above, anchoring members 114 are used to couple the distractor 100 to adjacent bone segments 116, 118. The anchoring member 114 includes a first footplate 150 coupling the outer sleeve 110 to the first bone segment 116 and a second footplate 152 coupling the inner member 112 to the second bone segment 118. The first and second footplates 150, 152 are sized and shaped to correspond to a surface of the first and second bone segments 116, 118, respectively. Each of the first and second footplates 150, 152 include an opening 154, 156 for receiving a bone screw to fix the first and second footplates 150, 152 to the first and second bone segments 116, 118, respectively. The location of each of the openings 154, 156 can be predetermined to lay over a portion of the first and second bone segments 116, 118 having an increased thickness and avoiding a blood vessel, nerve, and tooth.

The inner member 112 and/or outer sleeve 110 move along the distraction path from a first position, where the first and second bone segments 116, 118 are in an initial, less aligned position (e.g., FIG. 1, 13A), to a second position where the first and second bone segments 116, 118 are in a more desired alignment (e.g., FIG. 3, 13B, 13C). It is desired that the distraction path be defined to prevent pathological condylar displacement between the first and second bone segments 116, 118. While moving between the first and second position, the inner member 112 and/or outer sleeve 110 move through various points in three-dimensional space along a helical-shaped distraction path. For example, movement between a reference point on the inner member 112 and a corresponding reference point on the outer sleeve 110 defines a helical path of movement. The movement is facilitated by translation of the inner member 112 along the outer sleeve 110. As illustrated in FIGS. 9-11, providing front and back views of the example distractor 100, the inner member 112 and the outer sleeve 110 are generally arc shape and each have a corresponding curvature in the X-Y orientation/plane (a plane generally parallel to the sagittal plane). Likewise, as provided in FIG. 12, the inner member 112 and outer sleeve 110 have corresponding curvatures in the X-Z orientation/plane (a plane generally parallel to the transverse plane). As a result, movement between the inner member 112 and outer sleeve 110 is along a helical-shaped distraction path through various three-dimensional coordinates between the initial and desired alignment of the first and second bone segments 116, 118. FIGS. 13A-13C illustrate movement of the inner member 112 and outer sleeve 110 along the helical-shaped distraction path between an initial alignment (FIG. 13A), intermediate alignment (FIG. 13B) and a final/desired alignment (FIG. 13C).

FIG. 14 provides a partial end perspective view of the distractor 100 of FIG. 9 illustrating the anti-rotation mechanism that limits rotational movement of the drive mechanism 120/worm gear 122. As illustrated in FIG. 14, the worm gear 122 is rotationally coupled to two arms 128, 130 projecting from/beyond the inferior surface of the outer sleeve 110. A locking member 132 is coupled to an end 134 of the worm gear 122 projecting through the arm 128 adjacent the lower end of the distractor 100. The locking member 132 is coupled to the end 134 of the worm gear 122 at a position along the longitudinal axis of the worm gear 122. As such, rotation of the worm gear 122 results in a corresponding rotation of the locking member 132. The locking member 132 is sized and configured to engage a corresponding engaging member 136 coupled to the arm 128 of the outer sleeve 110. Engagement between the locking member 132 and the engaging member 136 prevents rotational movement of the worm gear 122.

The engaging member 136 can be formed from a compliant material where engagement/contact between the locking member 132 causes the engaging member 136 to bend or flex in response to the input force provided by the locking member 132. When the input force provided by the locking member 132 corresponds to the maximum bend/flex threshold of the engaging member 136, further rotational movement of the locking member 132 and worm gear 122 is resisted/prevented. As illustrated in FIG. 14, the engaging member 136 can include a bow spring/arc spring, where the input force of the locking member 132 is generally applied at the center of the arc. The locking member 132 can also include a structure having any regular or non-regular non-circular shape in cross-section such that at least a portion of the locking member 132 has an increased thickness with respect to the longitudinal axis of the driving mechanism 120/worm gear 122. As the locking member 132 rotates, the portion(s) of increased thickness provide increased input force onto the engaging member 136, the engaging member 126 in turn provides increased opposing force resisting/preventing rotation of the locking member 132, and as a result the worm gear 122.

Figure 15:
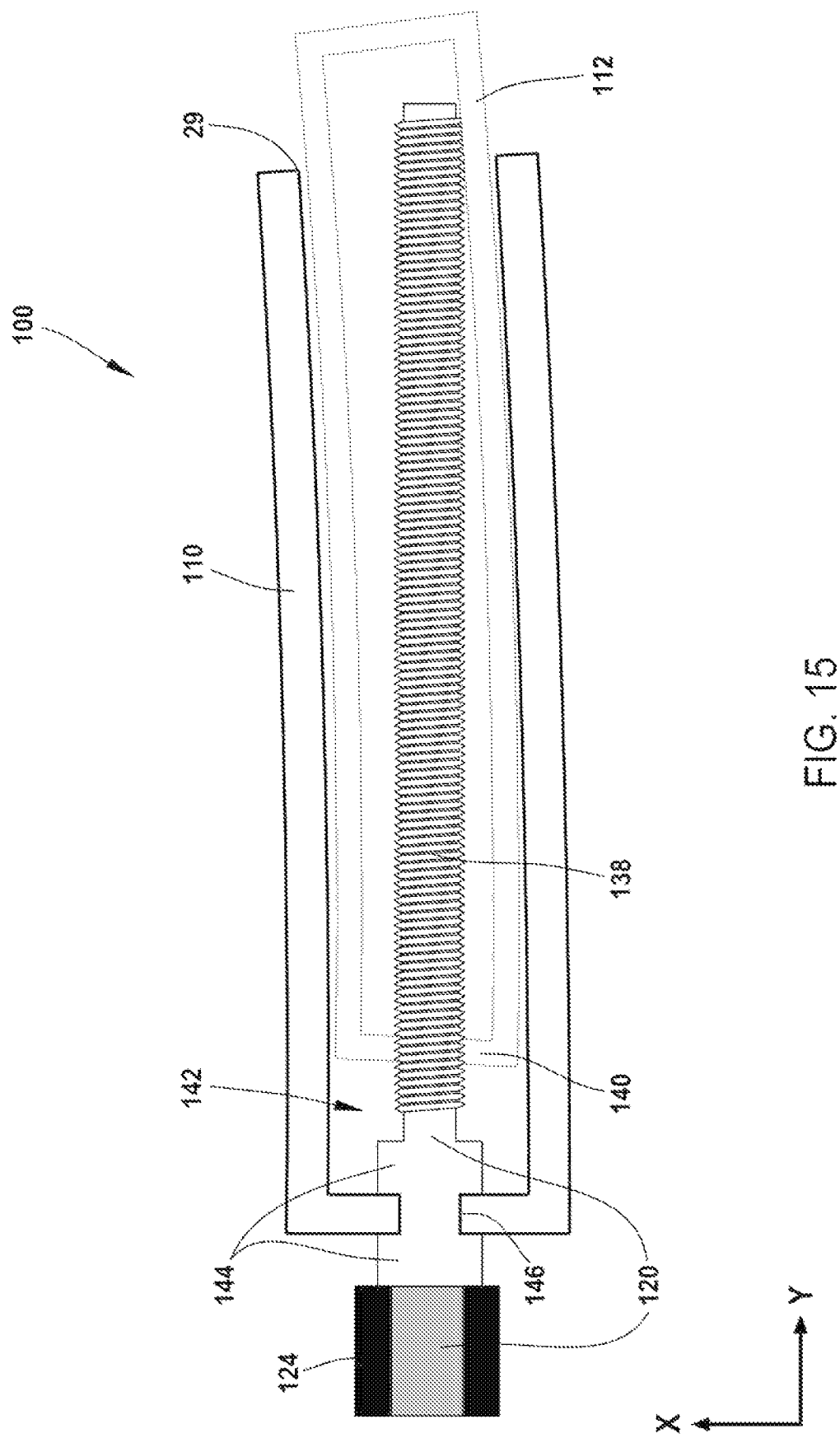
FIG. 15 is a side cross-section view of an example distraction device.
Figure 16:
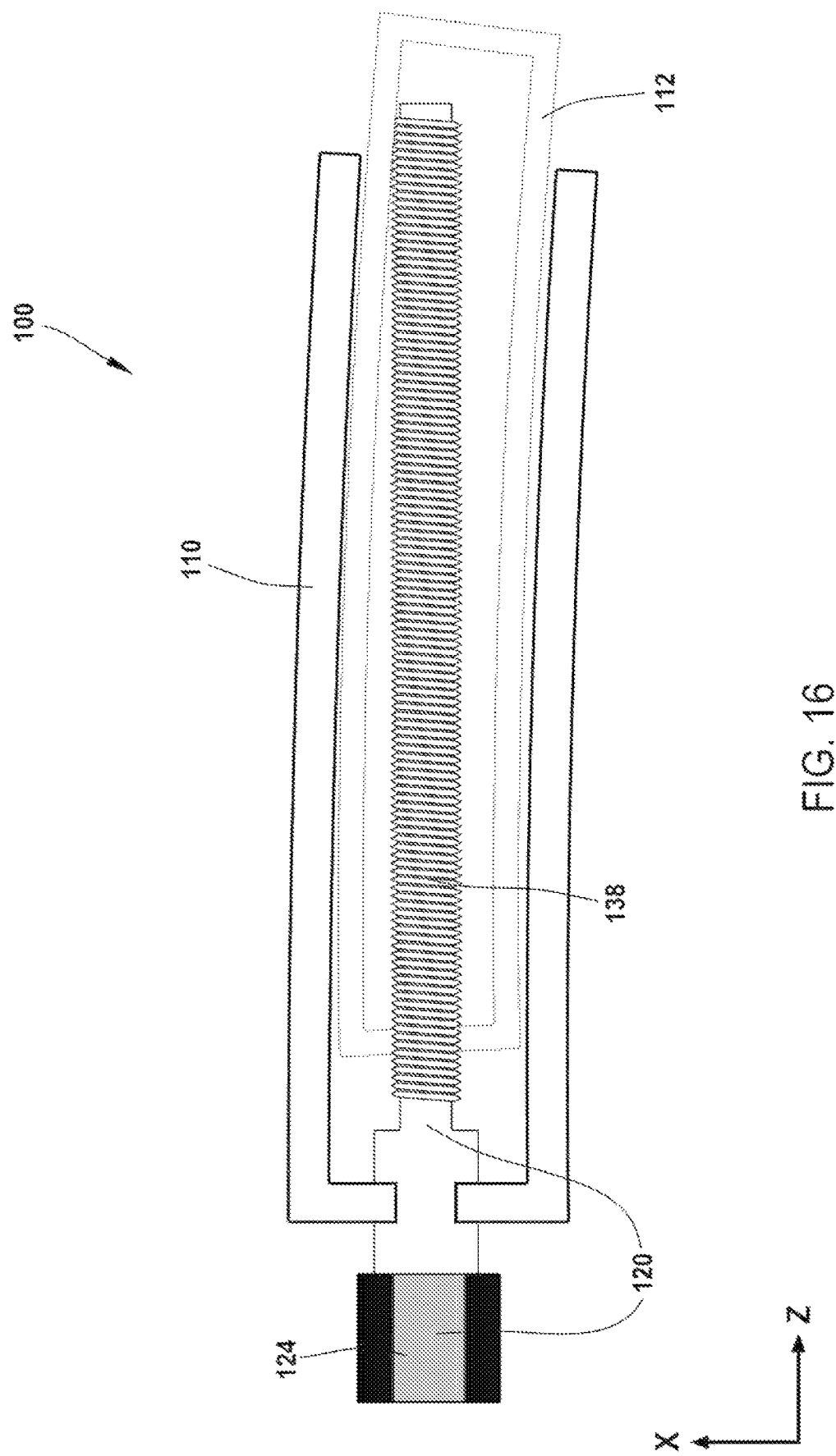
FIG. 16 is a top cross-section view of the distraction device of FIG. 15.

FIG. 15 is a side cross-sectional view of another embodiment of a telescoping distractor 100 including another example drive mechanism, and FIG. 16 is a side cross-sectional view of the distractor 100 of FIG. 15. FIG. 15 illustrates the telescoping helical distractor of FIG. 8 including a flexible screw style of driving mechanism. The steering apparatus of the distractor 100 includes an outer sleeve 110, a telescoping inner member 112, and a flexible screw 138 extending within the inner member 112 and rotatably coupled to the outer sleeve 110. The flexible screw 138 is threadably coupled to the inner member 112 and rotates freely with respect to the outer sleeve 110. A threaded opening 140 at the proximal end of the inner member 112 engages the threads of the flexible screw 138, such that rotation of the flexible screw 138 causes the inner member 112 to translate along the outer sleeve 110 and along the helical-shaped distraction path. The proximal end 142 of the flexible screw 138 includes a shoulder 144 for rotatably engaging an opening 146 at a proximal end of the outer sleeve 110.

The drive mechanism 120 can include an activation port 124 for receiving the rotational input forces that drive rotation of the flexible screw 138. As illustrated in FIG. 15, the activation port 124 is provided at the proximal end of the flexible screw 138 aligned with longitudinal axis of the flexible screw 138, such that the activation port 124 is axially aligned with the rotational axis of the flexible screw 138. The activation port 124 can be releasably coupled to the flexible screw 138. It is also contemplated that the activation port 124 can be fixedly coupled to the flexible screw 138 or integrally formed with the flexible screw 138. Like the distractor of FIG. 9, an activating/extension arm can be coupled to the drive mechanism 120 at the activation port 124 where rotation of the extension arm provides the input rotation to the drive mechanism 120/flexible screw 138 and the corresponding driving movement of the inner member 112 and outer sleeve 110 along the distraction path. It is contemplated that the extension arm can be coupled to the activation portion 124 at a universal joint-type coupling.

Though not illustrated in the section view, the distractor 100 of FIG. 15, the distractor 100 includes anchoring members 114 used to couple the distractor 100 to adjacent bone segments 116, 118. It is contemplated that either of the outer sleeve 110 or inner member 112 can be coupled to the mobile or stationary bone segment. As described above, to prevent bacteria from infecting the wound where the activation port 124/extension arm pass through the skin, the outer member outer sleeve 110 can be coupled to the stationary bone segment and the inner member 112 can be coupled to the mobile second bone segment. It is also contemplated both the first and second bone segments 116, 118 may be mobile, in which case coupling of the inner member 112 and outer sleeve 110 to their respective bone segments may be determined based on patient anatomy and desired outcome.

As described above, the inner member 112 and/or outer sleeve 110 move along the distraction path from a first position, where the first and second bone segments 116, 118 are in an initial, less aligned position (e.g., FIG. 1, 13A), to a second position where the first and second bone segments 116, 118 are in a more desired alignment (e.g., FIGS. 3, 13B, 13C). It is desired that the distraction path be defined to prevent pathological condylar displacement between the first and second bone segments 116, 118. While moving between the first and second position, the inner member 112 and/or outer sleeve 110 move through various points in three-dimensional space along a helical-shaped distraction path. For example, movement between a reference point on the inner member 112 and a corresponding reference point on the outer sleeve 110 defines a helical path of movement. The movement is facilitated by translation of the inner member 112 along the outer sleeve 110. As illustrated in FIG. 15, providing side cross-section view of the example distractor 100, the inner member 112 and the outer sleeve 110 are generally arc shape and each have a corresponding curvature in the X-Y orientation/plane. Likewise, as provided in FIG. 16, the inner member 112 and outer sleeve 110 have corresponding curvatures in the X-Z orientation/plane (a plane generally parallel to the sagittal plane). As a result, movement between the inner member 112 and outer sleeve 110 is along a helical-shaped distraction path through various three-dimensional coordinates between the initial and desired alignment of the first and second bone segments.

Figure 17:
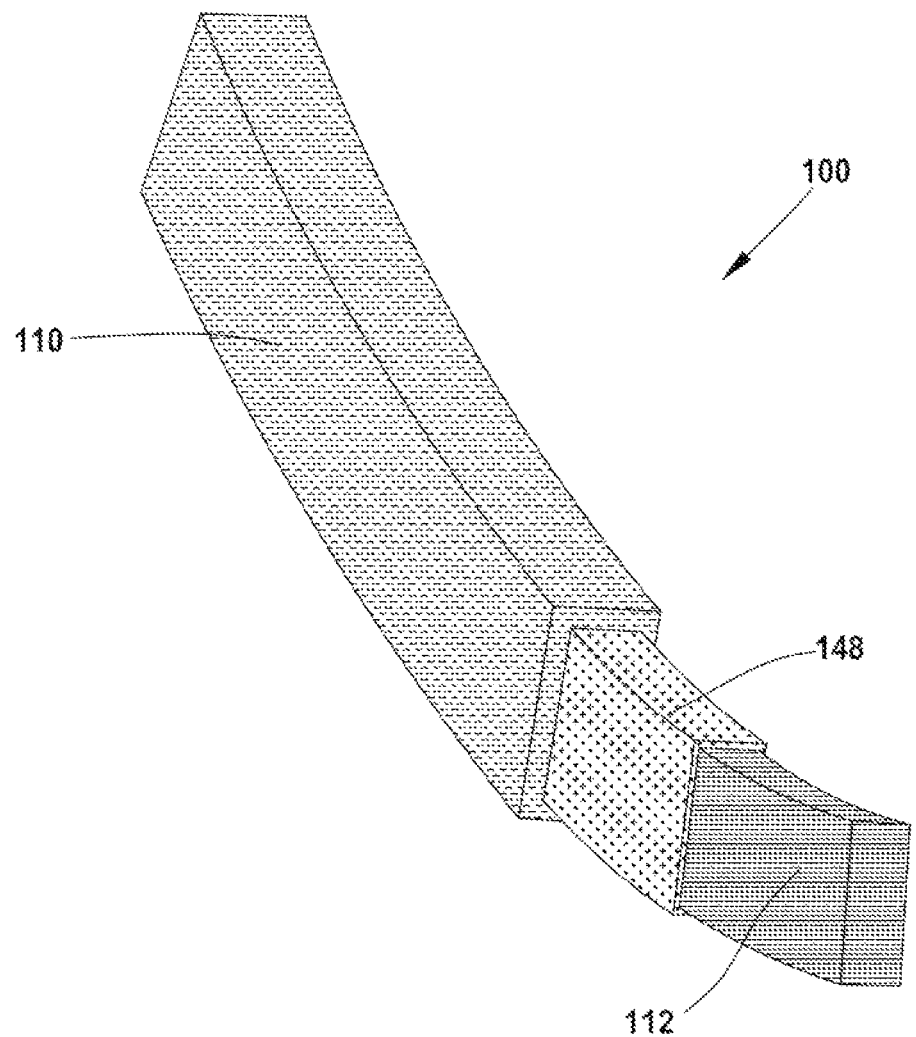
FIG. 17 is a side perspective view of the distraction device of FIG. 8 including an intermediate sleeve.

As illustrated in FIG. 8 (and FIGS. 9, 15), the steering apparatus includes an outer sleeve 110 and a telescoping inner member 112 that extends from/through an opening provided in the end of the outer sleeve 110. It is further contemplated that the distractor 100, can include an intermediate sleeve extending between the inner member 112 and outer sleeve 110. For example, as illustrated in FIG. 17, an intermediate sleeve 148 extending between the outer sleeve 110 and the inner member 112. The intermediate sleeve 148 extends from a distal opening provided in the outer sleeve 110 and the inner member 112 extends from a distal opening provided in the intermediate sleeve 148. Movement of the steering apparatus along the distraction path causes the intermediate sleeve 148 to further extend from the distal opening of the outer sleeve 110 and also causes the inner member 112 to further extend from the distal opening of the intermediate sleeve 148. The distractor 100 can include a two-stage driving mechanism 120, where a flexible screw extends within each of the inner member 112, intermediate sleeve 148 and outer sleeve 112. The flexible screw can be threadably coupled to the inner member 112 and intermediate sleeve 148 and rotatably coupled to the outer sleeve 110 such that the screw rotates freely with respect to the outer sleeve 110. Threaded openings at the proximal end of the inner member 112 and intermediate sleeve 148 engage the threads of the flexible screw, and rotation of the flexible screw causes the inner member 112 and the intermediate sleeve 148 to translate along the outer sleeve 110 and along the helical-shaped distraction path.

As illustrated in each of FIGS. 8-17, the outer sleeve 110 and the inner member 112 (and the intermediate sleeve 148) define a generally rectilinear cross-sectional shape. It is also contemplated that the outer sleeve 110 and the inner member 112 (and the intermediate sleeve 148) may also define a generally circular cross-sectional shape.

Figure 18A:
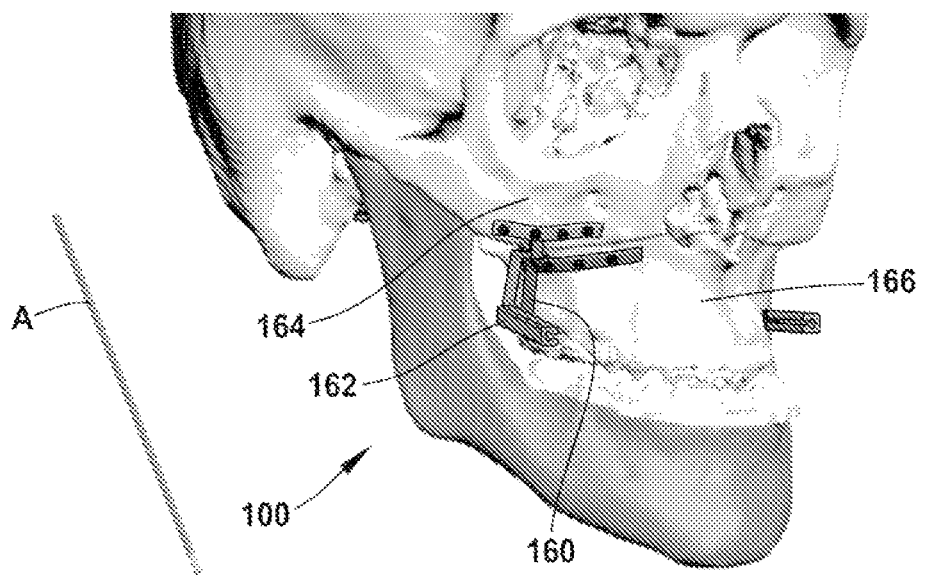
FIG. 18A is a perspective view of an anatomical model including an example distraction device where the patient's anatomy is illustrated in an initial alignment.
Figure 18B:
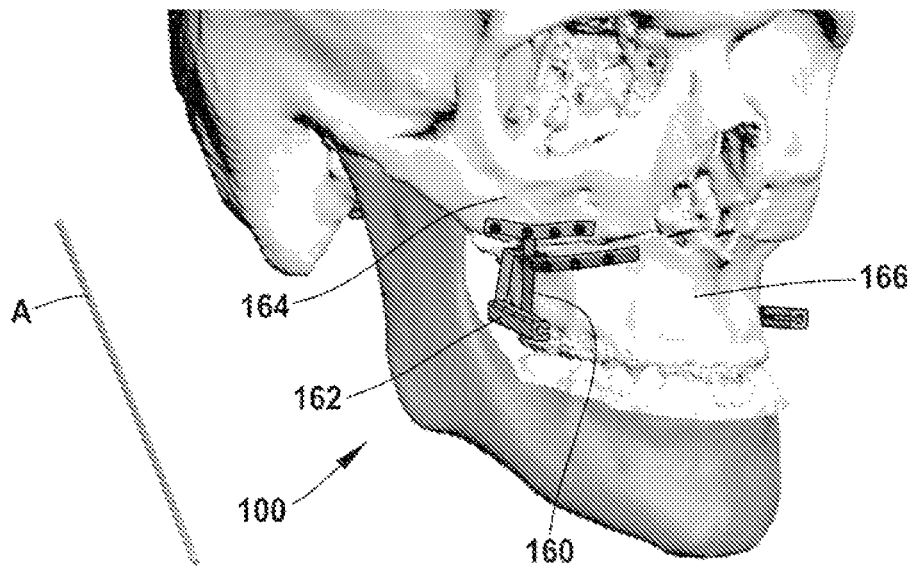
FIG. 18B is a perspective view of an anatomical model including the distraction device of FIG. 18A where the patient's anatomy is illustrated in an intermediate alignment.
Figure 18C:
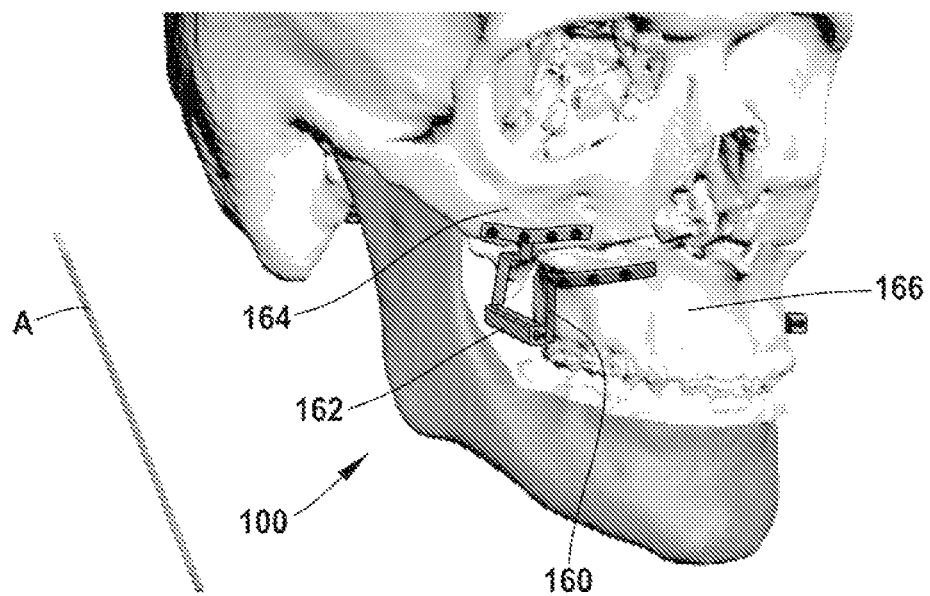
FIG. 18C is a perspective view of an anatomical model including the distraction device of FIG. 18A where the patient's anatomy is illustrated in a final/desired alignment.

FIG. 18A is a perspective view of another example orthopedic craniofacial distractor 100 illustrated on an anatomical model of a patient's skull with the facial bones in an initial alignment. FIG. 18B illustrates an intermediate alignment and FIG. 18C illustrates a final/desired alignment. The distractor 100 comprises a steering apparatus that directs movement of the distractor 100 along a helical-shaped distraction path. The steering apparatus includes a carriage member 160 slidingly coupled to a rail member 162. Movement of the carriage member 160 with respect to the rail member 162 is along a helical-shaped distraction path creates a gap/alignment between the first bone segment 164 (upper segment of the maxilla) and the second bone segment 166 (lower segment of the maxilla). Axis A identifies the axis of rotation of the helical-shaped distraction path.

Figure 19:
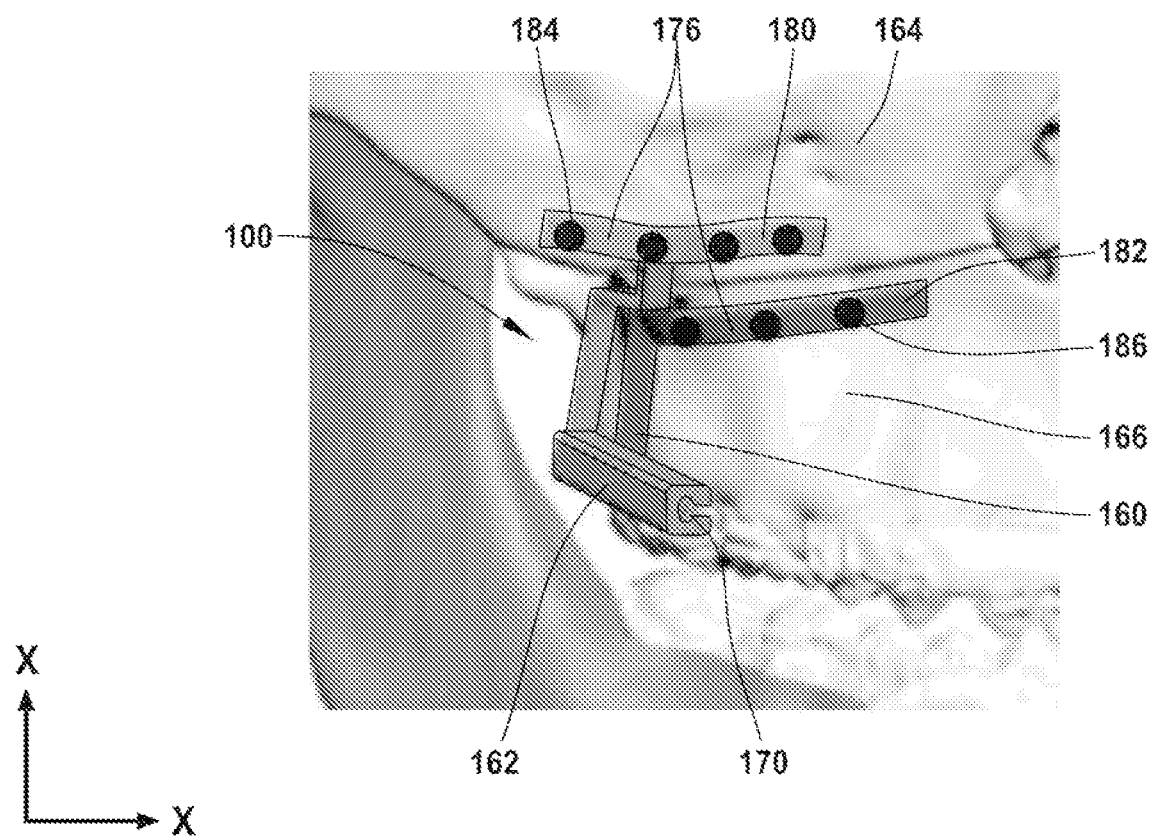
FIG. 19 is a partial close-up of FIG. 18A.
Figure 20:
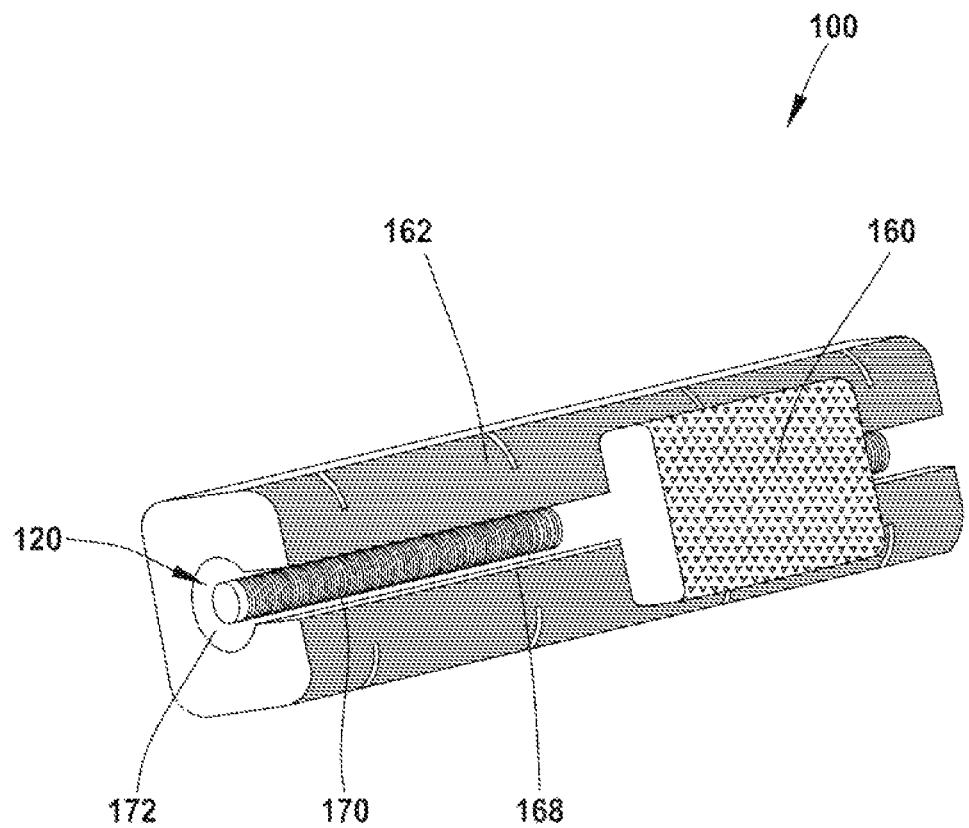
FIG. 20 is a side perspective view of the distraction device of FIG. 18.
Figure 22:
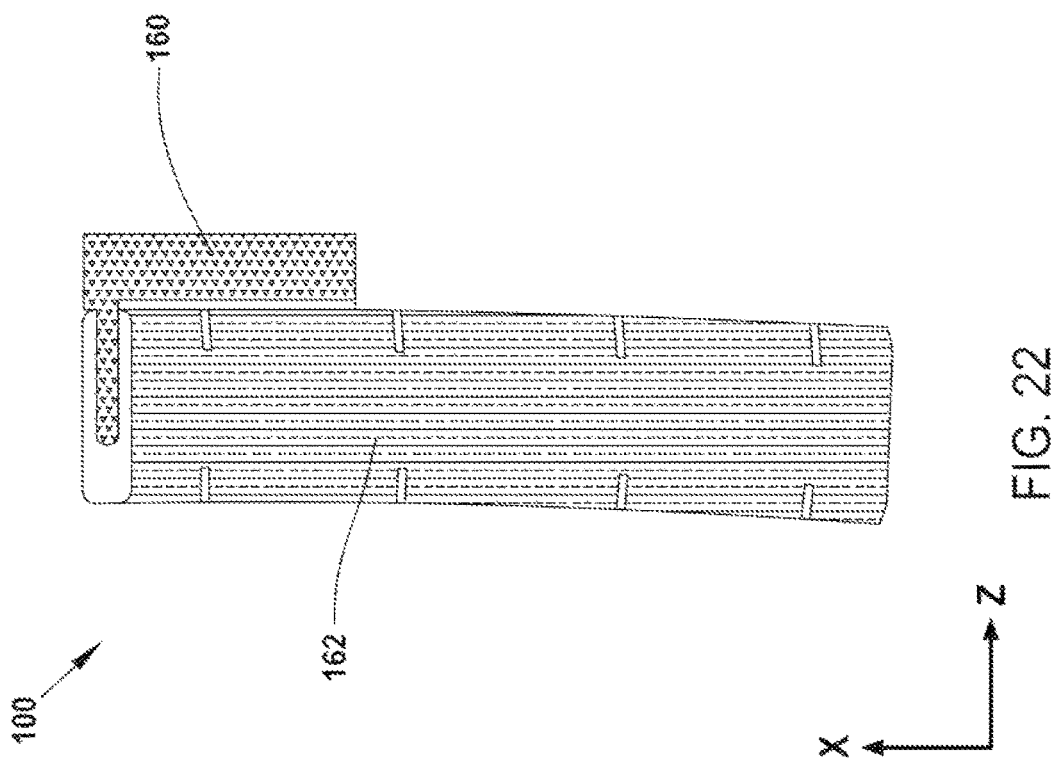
FIG. 22 is a top perspective view of the distraction device of FIG. 18.
Figure 21:
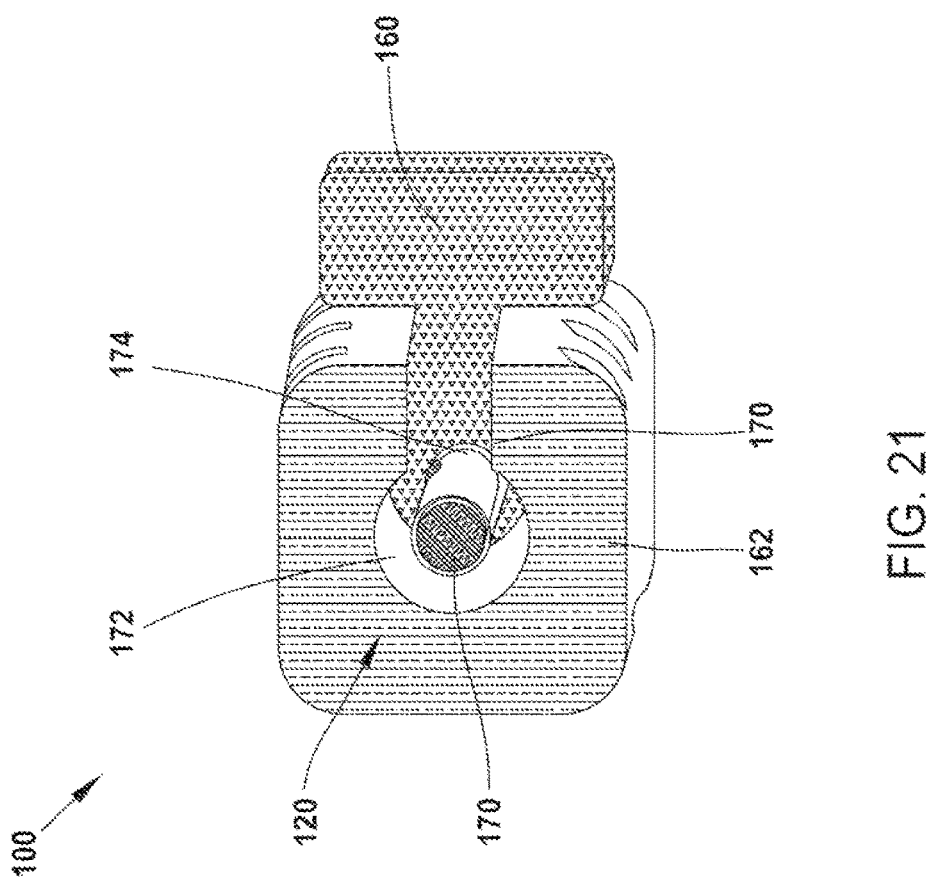
FIG. 21 is an end perspective view of the distraction device of FIG. 18

FIG. 19 is a close-up of the perspective view provided in FIG. 18A. FIG. 20 is a side perspective view, FIG. 21 is an end perspective view, and FIG. 22 is a top perspective view of the of the steering mechanism of the distractor 100 illustrated in FIG. 19. As provided in FIGS. 19-22, the carriage member 160 is slidingly coupled to the rail member 162 along a groove 168 defining the distraction path. The distraction drive mechanism 120 includes flexible screw 170 extending within a central opening 172 of the rail member 162. The flexible screw 170 also engages a threaded opening 174 extending through the carriage member 160 such that rotation of the flexible screw 170 causes a corresponding movement of the carriage member 160 with respect to the rail member 162 along the distraction path. The flexible screw 170 is retained within and rotates freely with respect to the rail member 162 while threadably engaging the threaded opening 174 provided on the carriage member 160.

The distraction drive mechanism 120 can include an activation port and extension arm for receiving the rotational input forces that drive rotation of the flexible screw 170. The activation port of the distraction drive mechanism 120 can be provided at an end of the rail member 162 an be axially aligned with the rotational axis of the flexible screw 170. The activation port can be releasably coupled to the flexible screw 170. It is also contemplated that the activation port can be fixedly coupled to or integrally formed with the flexible screw 170. Like the distractor of FIG. 9, an activating/extension arm can be coupled to the drive mechanism 120 at the activation port where rotation of the extension arm provides the input rotation to the drive mechanism 120/flexible screw 170 and the corresponding driving movement of the carriage member 160 with respect to the rail member 162 along the distraction path. It is contemplated that the extension arm can be coupled to the activation portion at a universal joint-type coupling.

As illustrated in FIGS. 18 and 19, anchoring members 176 couple the distractor 100 to the adjacent bone segments 164, 166. The anchoring members 176 including a first footplate 180 for coupling the rail member 162 to the first bone segment 164 and a second footplate 182 for coupling the carriage member 160 to the second bone segment 166. The first and second footplates 180, 182 are sized and shaped to correspond to a surface of the first and second bone segments 164, 166, respectively. Each of the first and second footplates 180, 182 include at least one opening 184, 186 for receiving a bone screw to fix the footplate to the first and second bone segments 164, 166, respectively. The location of each of the openings 184, 186 is predetermined to lay over a portion of the first and second bone segment 164, 166 having an increased thickness and avoiding a blood vessel, nerve, and tooth. It is contemplated that either of the carriage member 160 or the rail member 162 can be coupled to a mobile or stationary bone segment. To prevent bacteria from infecting the wound where the activation port/extension arm pass through the skin, the rail member 162 can be coupled to the stationary bone segment and the carriage member 160 can be coupled to the mobile second bone segment. It is also contemplated both the first and second bone segments 164, 166 may be mobile, in which case coupling of the carriage member 160 and the rail member 162 to their respective bone segments may be determined based on patient anatomy and desired outcome.

As described above, the carriage member 160 and/or rail member 162 move along the distraction path from a first position, where the first and second bone segments 164, 166 are in an initial, less aligned position (e.g., FIG. 18A), to a second position where the first and second bone segments 164, 166 are in a more desired alignment (e.g., FIGS. 18B, 18C). It is desired that the distraction path be defined to prevent pathological condylar displacement between the first and second bone segments 164, 166. While moving between the first and second position, the carriage member 160 and/or rail member 162 move through various points in three-dimensional space along a helical-shaped distraction path. For example, movement between a reference point on the carriage member 160 and a corresponding reference point on the rail member 162 defines a helical path of movement. The movement is facilitated by translation of the carriage member 160 along the groove 168 provided on the rail member 162. As illustrated in FIG. 19, providing side perspective view of the example distractor 100, the rail member 162 can have a curvature in the X-Y orientation/plane (a plane generally parallel to the sagittal plane). Likewise, as provided in FIG. 22, the rail member 162 can have a curvature in the X-Z orientation/plane (a plane generally parallel to the transverse plane). As a result, movement between the carriage member 160 and the rail member 162 is along a helical-shaped distraction path through various three-dimensional coordinates between the initial and desired alignment of the first and second bone segments 164, 166.

Figure 23A:
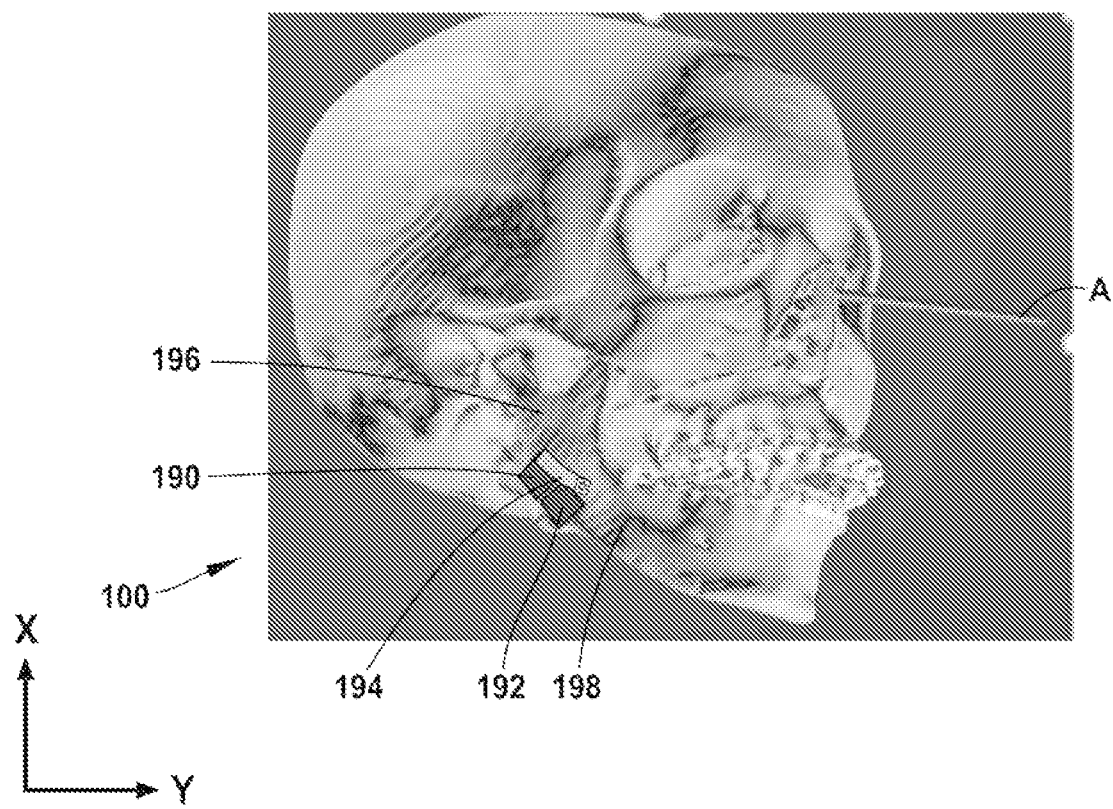
FIG. 23A is a perspective view of an anatomical model including an example distraction device where the patient's anatomy is illustrated in an initial alignment.
Figure 23B:
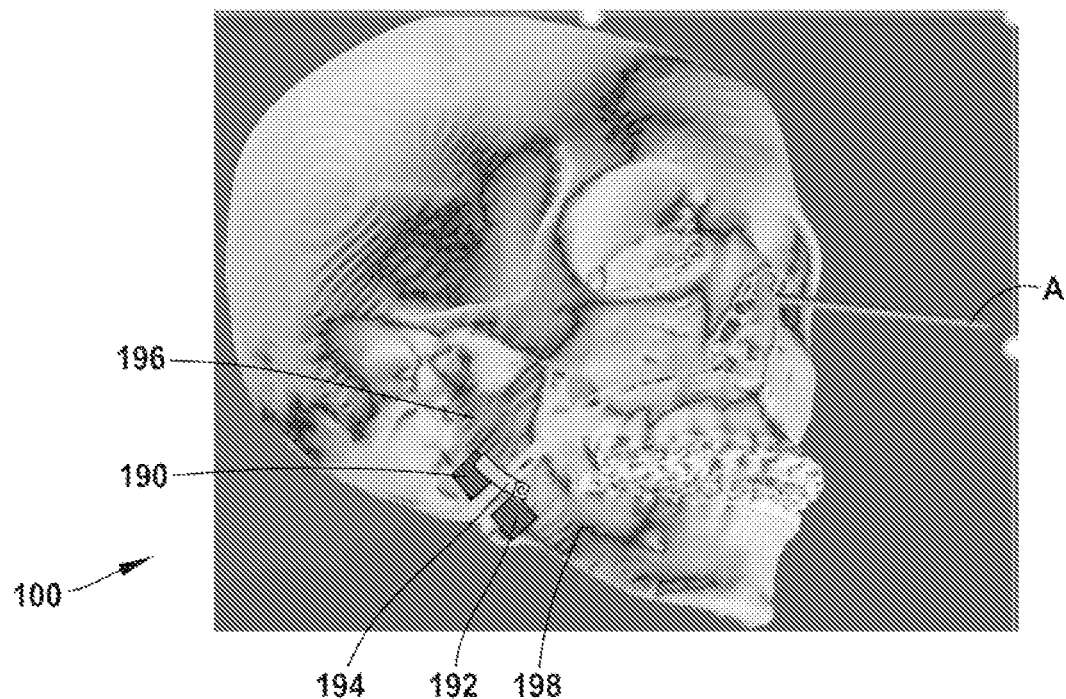
FIG. 23B is a perspective view of an anatomical model including the distraction device of FIG. 23A where the patient's anatomy is illustrated in an intermediate alignment.
Figure 23C:
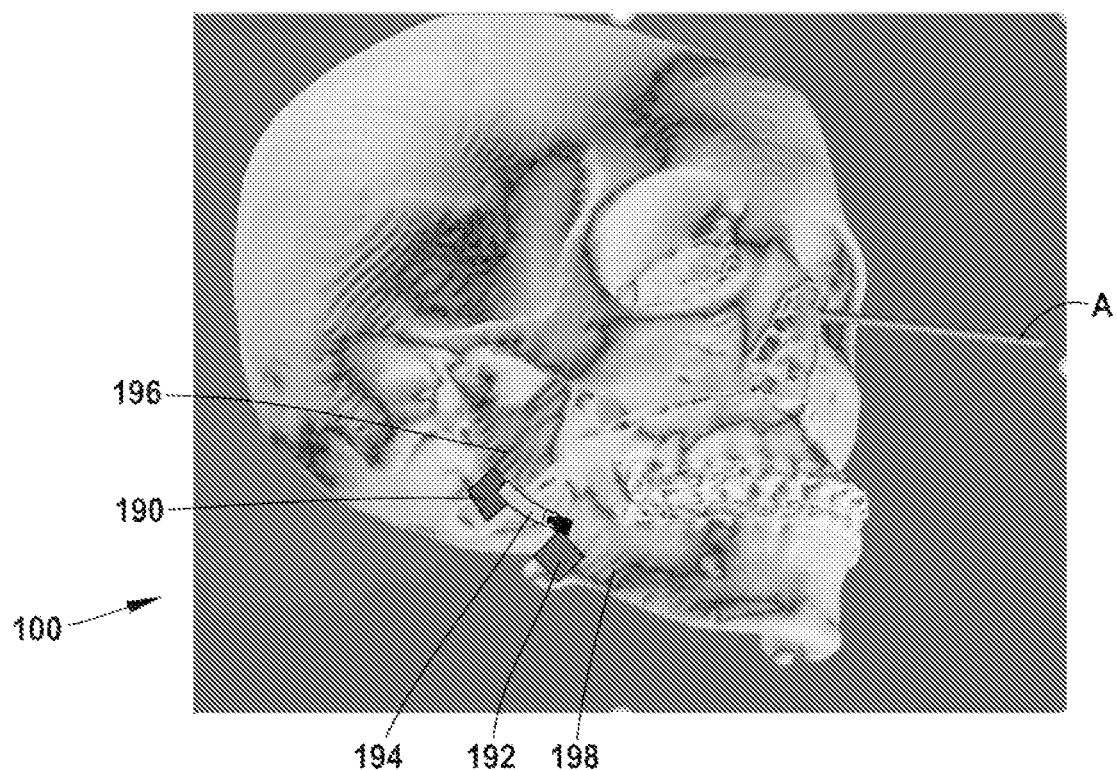
FIG. 23C is a perspective view of an anatomical model including the distraction device of FIG. 23A where the patient's anatomy is illustrated in a final/desired alignment.
Figure 24A:
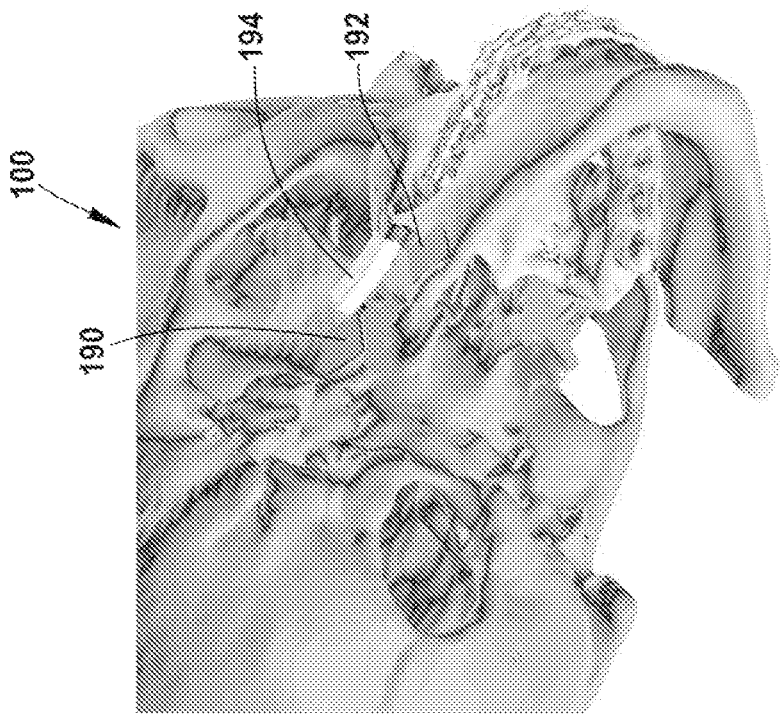
FIG. 24A is a bottom perspective view of an anatomical model including the distraction device of FIG. 23A where the patient's anatomy is illustrated in an initial alignment.
Figure 24B:
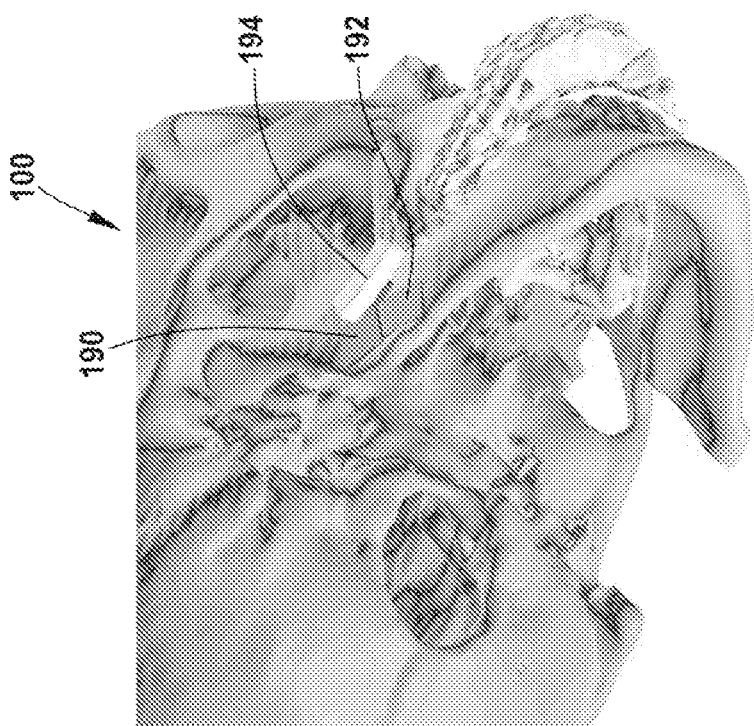
FIG. 24B is a bottom perspective view of an anatomical model including the distraction device of FIG. 23A where the patient's anatomy is illustrated in a final/desired alignment.
Figure 25B:
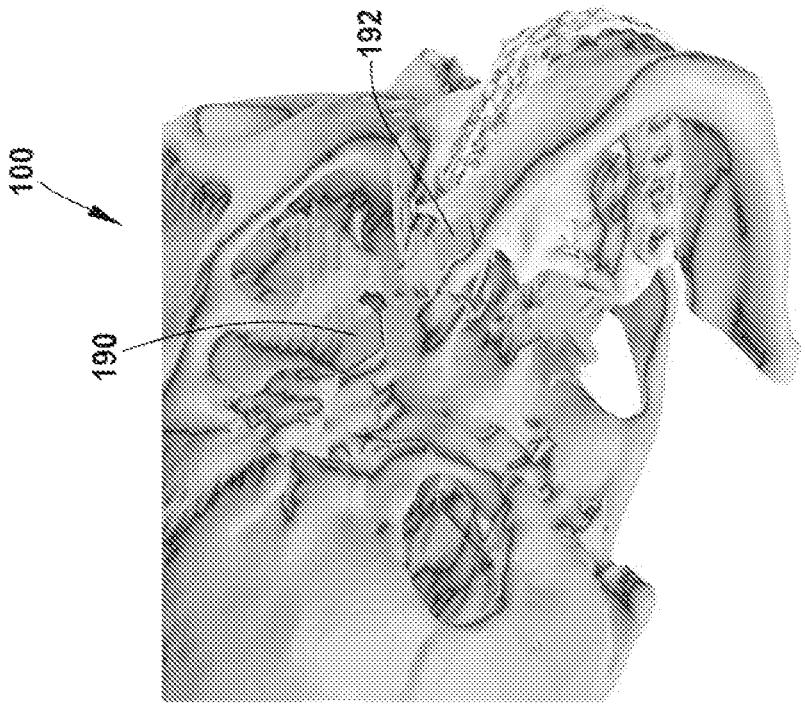
FIG. 25B is a bottom perspective view of an anatomical model including the distraction device of FIG. 23A (with the rail member removed) where the patient's anatomy is illustrated in a final/desired alignment.
Figure 25A:
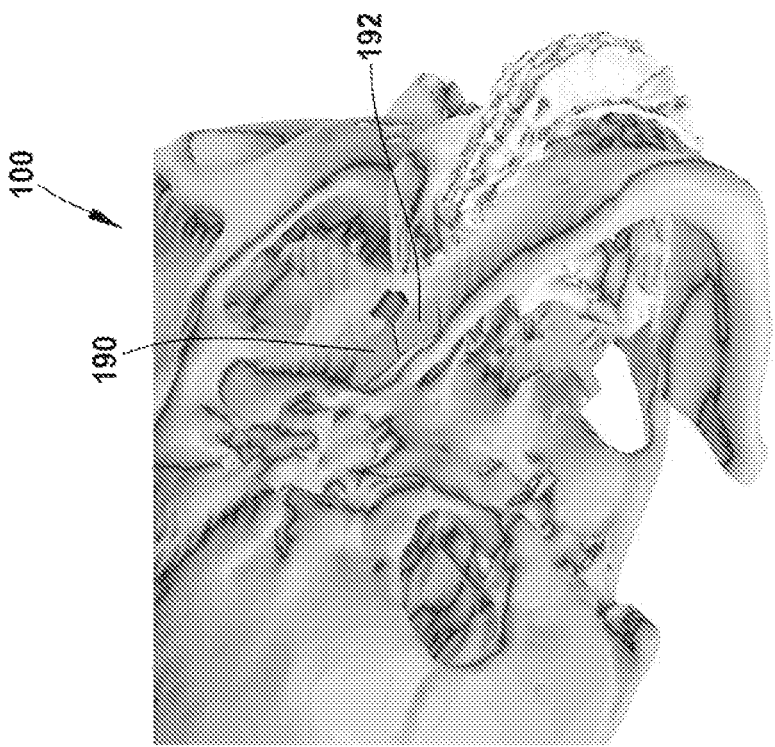
FIG. 25A is a bottom perspective view of an anatomical model including the distraction device of FIG. 23A (with the rail member removed) where the patient's anatomy is illustrated in an initial alignment.

FIG. 23A is a perspective view of another example orthopedic craniofacial distractor 100 illustrated on an anatomical model of a patient's skull with the facial bones in an initial alignment. FIG. 23B illustrates an intermediate alignment and FIG. 23C illustrates a final/desired alignment. FIGS. 24A and 24B provide a bottom perspective view of the distractor 100 with the facial bones in an initial alignment and final/desired alignment, respectively. FIGS. 25A and 25B correspond to FIGS. 24A and 24B, except that the rail member is not illustrated.

The distractor 100 comprises a steering apparatus that directs movement of the distractor 100 along a helical-shaped distraction path. The steering apparatus includes a first carriage member 190 and second carriage member 192, each slidingly coupled to a rail member 194. Movement of the first and second carriage members 190, 192 with respect to the rail member 194 is along the helical-shaped distraction path creates a gap and alignment between the first bone segments 196 (upper segment of the mandible) and the second bone segment 198 (lower segment of the mandible). Axis A identifies the axis of rotation of the helical-shaped distraction path.

Figure 27:
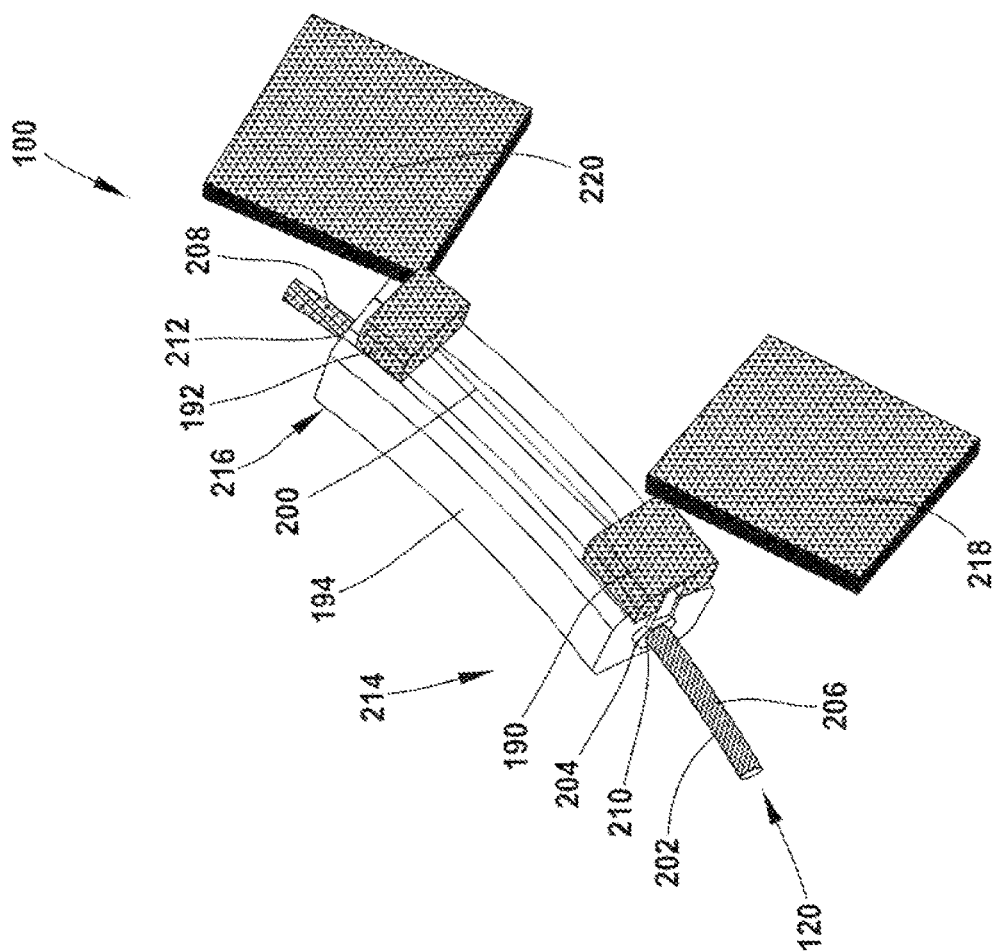
FIG. 27 is a side perspective view of the distraction device of FIG. 23.
Figure 26:
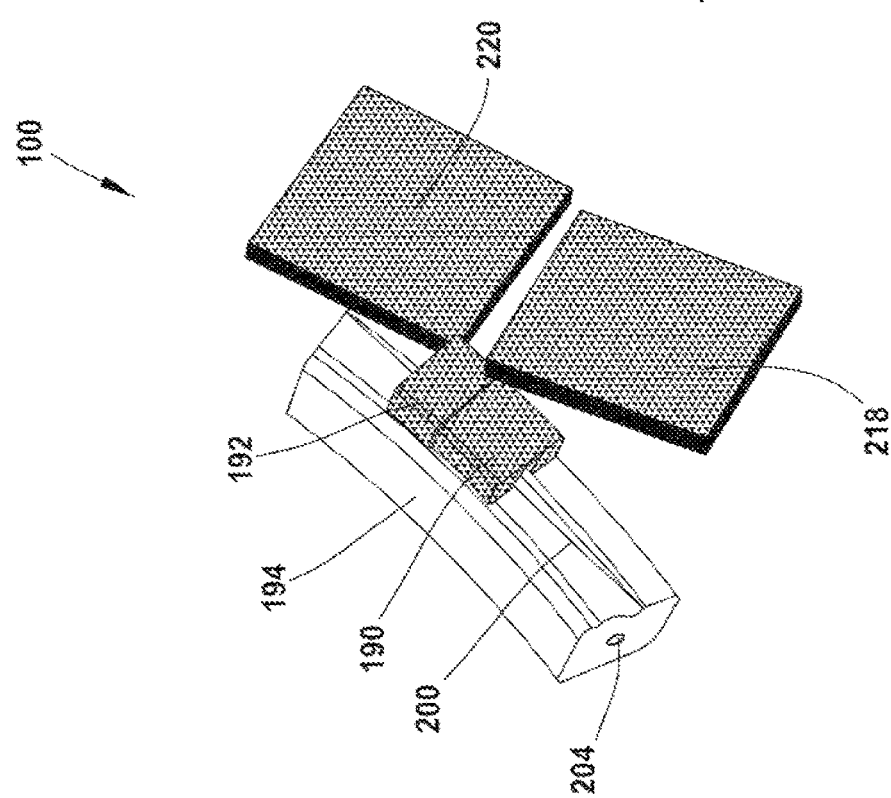
FIG. 26 is a side perspective view of the distraction device of FIG. 23.

FIG. 26 is a side perspective view of the steering mechanism of the distractor illustrated in FIG. 23 where the first and second carriage member 190, 192 are in an initial configuration and not spaced (or are minimally spaced) apart along the rail member 194. FIG. 27 is a side perspective view of the steering mechanism of the distractor where the first and second carriage member 190, 192 are spaced apart along the rail member 194. As provided in FIGS. 23-27, the first and second carriage members 190, 192 are slidingly coupled to the rail member 194 along a groove 200 defining the distraction path. The distraction drive mechanism 120 includes a flexible screw 202 extending within a central opening 204 of the rail member 162. The flexible screw 202 rotates freely with respect to the rail member 194 and can also be retained within the rail member 194. The flexible screw 202 can include two threaded portions having different orientations, pitch, diameter, shape, etc. for separately engaging the first and second carriage members 190, 192. For example, the flexible screw 202 can include a first portion 206 and a spaced apart second portion 208. The first and second portions 206, 208 can vary in orientation, pitch, diameter and/or thread shape, where the varied thread structure corresponds to the threaded openings provided in the first and second carriage members 190, 192, respectively. For example, the first portion 206 can have a clockwise orientation and the second portion 208 can have a counter-clockwise orientation, where the threads of the first portion 206 correspond with the threaded opening 210 provided in the first carriage 190 and the threads of the second portion 208 correspond with the threaded opening 212 provided in the second carriage 192.

As illustrated in FIGS. 26 and 27, because the flexible screw has two different thread structures for separately engaging the first and second carriage members 190, 192, the first and second carriage members 190, 192 can be movable along the rail member 194 is directions away from each other. For example, FIG. 26 illustrates the first and second carriage members 190, 192 in an initial, adjacent, configuration. Rotation of the flexible screw 202 causes the first and second thread portions 206, 208 to separately engage the first and second carriage members 190, 192. In the example described above, because the first and second thread portions 206, 208 have different orientations (clockwise vs. counterclockwise), rotation of the flexible screw 202 causes the first and second carriage members 190, 192 to move from the initial/adjacent position (between the proximal end 214 and distal end 216 of the rail member 194) away from each other in a direction towards the opposing ends of the rail member 194. As illustrated in FIG. 27, the first carriage member moves from the initial intermediate position in a direction generally towards the proximal end 214 of the rail member 194, and the second carriage member 192 moves from the initial intermediate position in a direction generally towards the distal end 216 of the rail member 194. It is contemplated the rail member 194 can direct movement of the first and second carriage members 190, 192 along the entire distraction distance of the distractor 100.

The activation port of the distraction drive mechanism 120 can be provided at an end of the rail member 194 an be axially aligned with the rotational axis of the flexible screw 202. The activation port can be releasably coupled to the flexible screw 202. It is also contemplated that the activation port can be fixedly coupled to or integrally formed with the flexible screw 202. Like the distractor of FIG. 9, an activating/extension arm can be coupled to the drive mechanism 120 at the activation port where rotation of the extension arm provides the input rotation to the drive mechanism 120/flexible screw 202 and the corresponding driving movement of the first and second carriage members 190, 192 with respect to the rail member 194 along the distraction path. It is contemplated that the extension arm can be coupled to the activation portion at a universal joint-type coupling.

As illustrated in FIGS. 23-27, anchoring members are used to couple the distractor 100 to the adjacent bone segments 196, 198. The anchoring members include a first footplate 218 for coupling the first carriage member 190 the first bone segment 196 and a second footplate 220 for coupling the second carriage member 192 to the second bone segment 198. The first and second footplates 218, 220 are sized and shaped to correspond to a surface of the first and second bone segments 196, 198, respectively. Each of the first and second footplates 218, 220 can include openings for receiving a corresponding bone screw to fix the footplate to the first and second bone segments 196, 198, respectively. The location of the openings can be predetermined to lay over a portion of the first and second bone segment 196, 198 having an increased thickness and avoiding a blood vessel, nerve, and tooth. It is contemplated that either of the first and second carriage members 190, 192 can be coupled to a mobile or stationary bone segment. To prevent bacteria from infecting the wound where the activation port/extension arm pass through the skin, the carriage member adjacent the activation port can be coupled to the stationary bone segment and the other carriage member can be coupled to the mobile second bone segment. It is also contemplated both the first and second bone segments 196, 198 may be mobile, in which case coupling of the first and second carriage members 190, 192 to their respective bone segments may be determined based on patient anatomy and desired outcome.

As described above, the first and second carriage members 190, 192 move along the distraction path from a first position, where the first and second bone segments 196, 198 are in an initial, less aligned position (e.g., FIGS. 23A, 24A, 25A), to a second position where the first and second bone segments 196, 198 are in a more desired alignment (e.g., FIGS. 23B, 23C, 24B, 25B). It is desired that the distraction path be defined to prevent pathological condylar displacement between the first and second bone segments 196, 198. While moving between the first and second position, the first and second carriage members 190, 192 through various points in three-dimensional space along a helical-shaped distraction path. For example, movement between a reference point on the first carriage member 190 (or second carriage member 192) and a corresponding reference point on the rail member 194 defines a helical path of movement. The movement is facilitated by translation of the first and second carriage members 190, 192 along the groove 200 provided on the rail member 194. As illustrated in FIGS. 23A-23C, 26, and 27, providing side perspective view of the example distractor 100, the rail member 194 can have a curvature in the X-Y orientation/plane (a plane generally parallel to the sagittal plane). Likewise, as provided in FIGS. 24A, 24B, the rail member 194 can have a curvature in the X-Z orientation/plane (a plane generally parallel to the transverse plane). As a result, movement of the first and second carriage members 190, 192 along the rail member 194 is along a helical-shaped distraction path through various three-dimensional coordinates between the initial and desired alignment of the first and second bone segments 196, 198.

Figure 28:
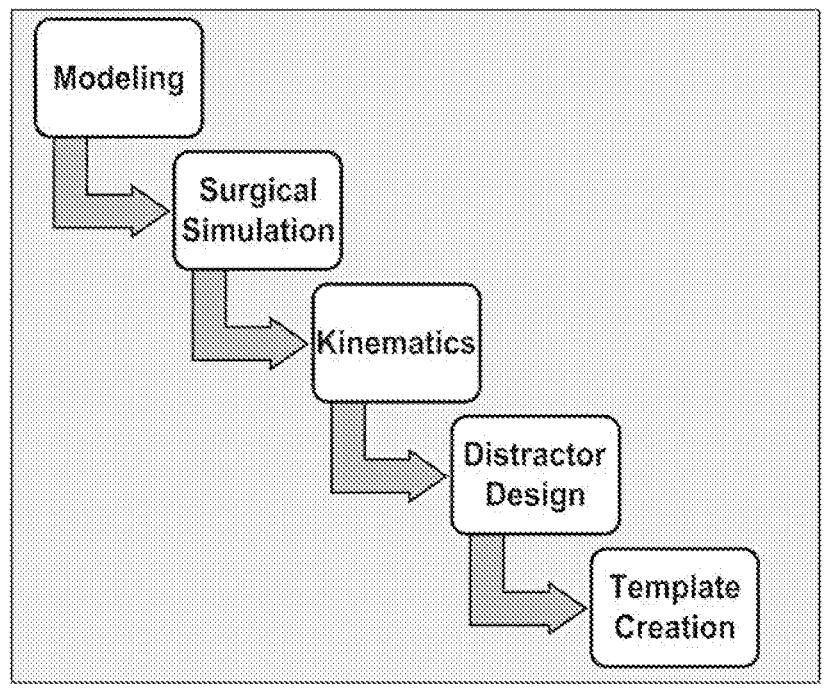
FIG. 28 is a flow diagram of an example method of designing and constructing a custom distraction device.

Next will be described a system and method for designing and constructing custom craniofacial distraction devices as described above. To ensure ideal patient outcomes, a distractor device custom to the patient anatomy and desired distraction path is required. The present system readily calculates the optimal path of motion for any patient, and automatically designs the main components of the distractor by guiding the user through patient modeling, surgical simulation, kinematics, distractor design, and template creation. FIG. 28 provides a flow diagram of the design and construction process. It is contemplated that the present system can be used to design and construct custom versions of any of the distraction devices discussed herein. For example, the present system can be utilized to design and construct a telescoping distraction device including, for example, a sleeve and telescoping member, where movement of the telescoping member is along the custom/determined helical-shaped distraction path. The constructed distraction device may also comprise a rail and carriage-type distraction device including, for example, a carriage member slidingly coupled to a rail member, where movement of the carriage member with respect to the rail member is along the custom/determined helical-shaped distraction path. The constructed distraction device may also comprise a rail and carriage-type distraction device including two carriage members slidingly coupled to the rail member, where movement of the two carriage members with respect to the rail member is along the custom/determined helical-shaped distraction path.

Figure 29:
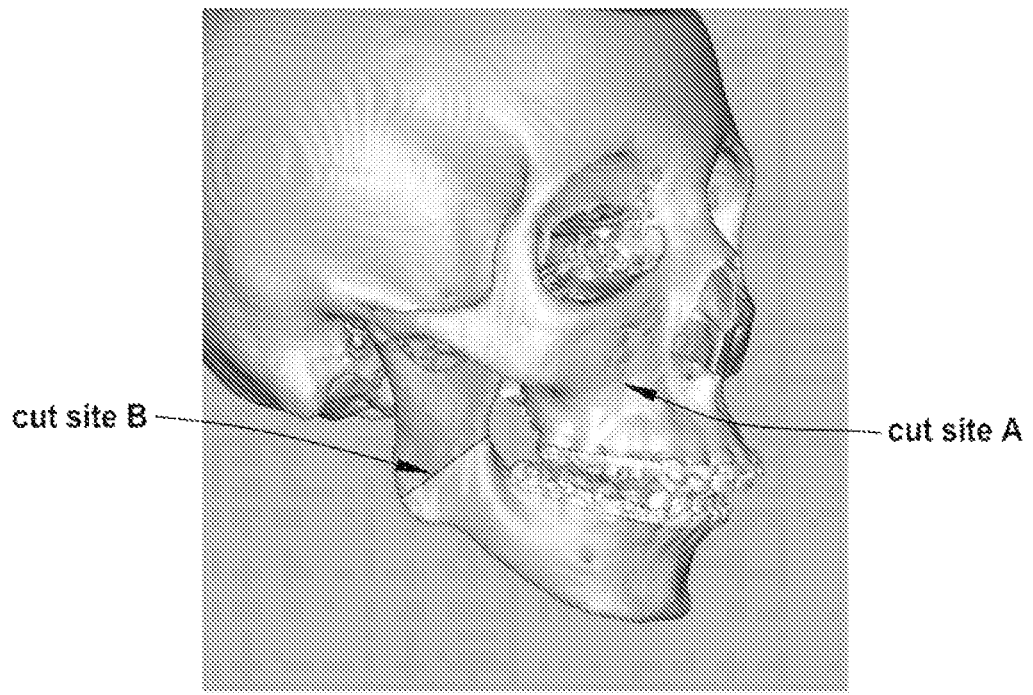
FIG. 29 is an example patient model in an initial alignment.

In the first step, modeling, an initial patient model is presented. The model comprises three-dimensional renderings of the patient's skull, the model is then provided to the operator for analysis via a control interface including a graphical user interface and an input interface for receiving operator input. One may build an accurate computer model of the patient's anatomy using data from medical images. For example, computer scans (CTs) and dental scans can be merged and segmented to build three-dimensional models of the patient's skull, teeth, nerves, and soft-tissues. In addition, an anatomical frame of reference can be added to the model. FIG. 29 provides an example patient model.

Figure 30:
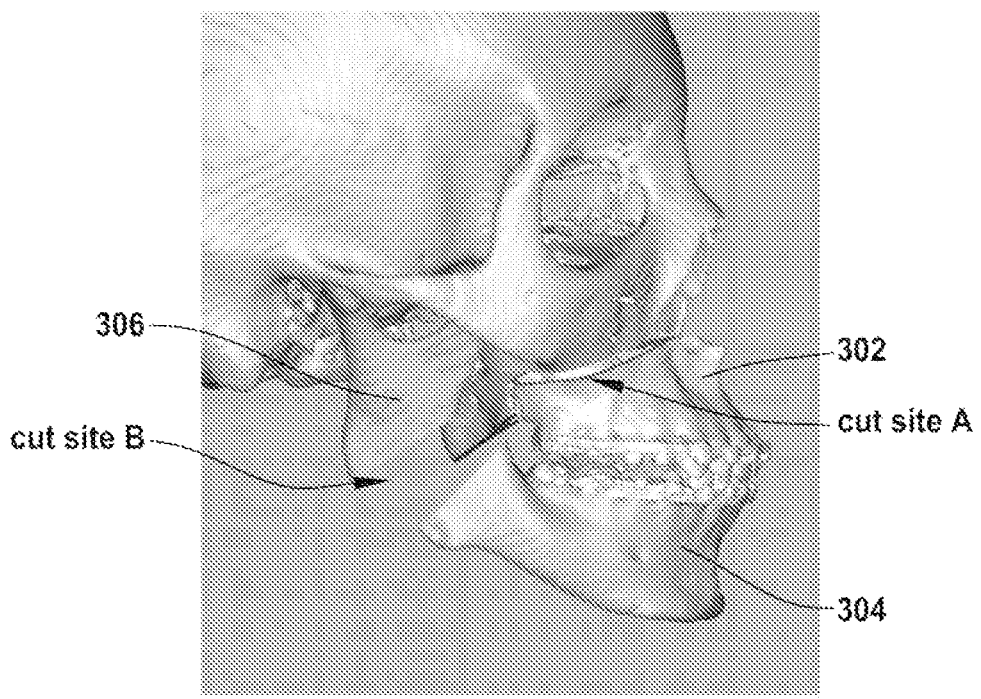
FIG. 30 is an example patient model in a final/desired alignment.
Figure 33:
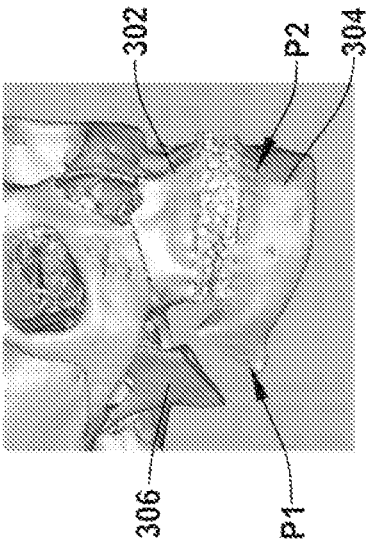
FIG. 33 is an example patient model in a final/desired alignment.
Figure 34:
FIG. 34 is an example patient model in a final/desired alignment.

In the next step, surgical simulation, the operator emulates a distraction treatment. He/she cuts the bone with a virtual knife and moves the bone segments into ideal alignment. FIG. 30 illustrates the patent model with the bone segments moved into an ideal alignment. For example, the system can receive an input corresponding to the operator's interaction with the control interface identifying a cut site (cut site A, cut site B) on the initial patent model for separating the model into corresponding bone segments. As illustrated in FIGS. 29 and 30, cut sites A and B are identified and the resulting first bone segment 302, second bone segment 304 and the third bone segment 305. Each of the first, second, and third bone segments 302, 304, 306 are then movable with respect to the others.

In the following step, kinematics, the system will analyze the motion of the bone segments (e.g., first, second, and third bone segments 302, 304, 306). Because the motion of the various bone segments is relative, the operator must first provide a frame of reference. The usual frame of reference is the Standard Anatomical Frame of Reference, a three-dimensional Cartesian system made by the sagittal, axial and coronal planes. In some circumstance, like in maxillary distraction, where a single segment is moving, the standard frame of reference works well. Yet in other circumstances, like in mandibular distraction, where two or more bone segments move, tracking the movements in the standard frame of reference can be difficult.

When all of the bone segments are moving/mobile, it is best to analyze the motion of each in relation to one of the segments. Accordingly, the present system can freeze a selected segment and capture the movement of the other segments in relation to the now static segment, thus simplifying the kinematic calculations. For example, in bilateral mandibular distraction, both proximal segments (first and second bone segments 302, 304) and the distal segment (third bone segment 306) may move, in relation to the anatomical frame of reference. Yet, the same movement is easier to track, if the distal segment 306 is held "stationary" and the proximal segments 302, 304 are moved in relation to it. Our distractor design system supports the use of multiple frames of reference. The system has a global coordinate system, as well as local coordinate systems for each object in the scene. The user can edit the local frames of reference, by relocating their origins and by reorienting their axes.

Figure 31:
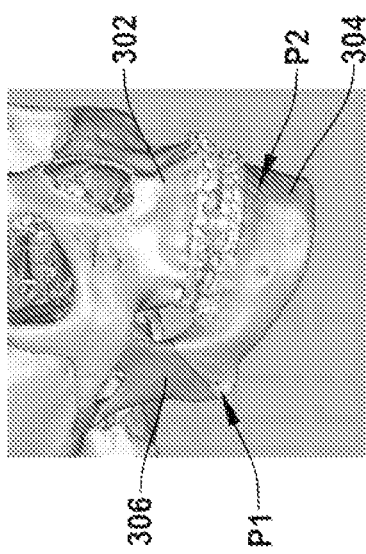
FIG. 31 is an example patient model in an initial alignment.
Figure 32:
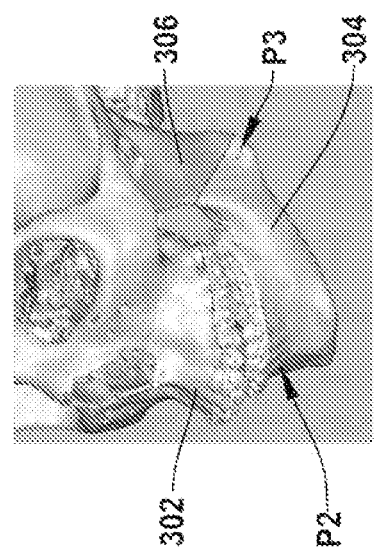
FIG. 32 is an example patient model in an initial alignment.

To calculate the helical path of motion for any moving segment, the operator selects (tags) various points/marker array on some or all of the bone segments 302, 304, 306. For example, in the present example as illustrated in FIGS. 31-34, the system receives this operator input at the control interface and identifying an initial position of a marker array associated with the second bone segment 304. The marker array including first marker (P1), a second marker (P2) and a third marker (P3) located on the second bone segment 304, where each marker has corresponding three-dimensional coordinates (x, y, z). FIGS. 31 and 32 illustrate example initial location of the first, second and third markers P1, P2, P3 in the initial alignment. While only three markers are identified in the present example, it is contemplated locations of additional markers may be used. Likewise, fewer markers (at least one) may be used.

The system records the three-dimensional coordinates of each marker of the marker array(s) when the segment(s) is in the original alignment (FIG. 29), and when the corresponding bone segment(s) is in final alignment (FIG. 30). Example coordinate data for the marker array of the second bone segment 304 (illustrated in FIGS. 29 and 30) is provided in the following tables. Similar marker array coordinate data can be determined for the marker arrays other bone segments (e.g., first bone segment 302 and third bone segment 306).

TABLE 1

Initial Alignment Data

| Anatomical: Mandible Reference | Value One | Value Two | Value Three |
|---|---|---|---|
| P1 | x: −45.7 mm | y: 117.4 mm | z: 62.3 mm |
| P2 | x: −0.2 mm | y: 61.0 mm | z: 49.1 mm |
| P3 | x: 47.0 mm | y: 114.1 mm | z: 60.8 mm |

TABLE 2

Final Alignment Data

| Anatomical: Mandible Reference | Value One | Value Two | Value Three |
|---|---|---|---|
| P1 | x: −44.3 mm | y: 102.8 mm | z: 50.2 mm |
| P2 | x: −0.8 mm | y: 43.5 mm | z: 50.2 mm |
| P3 | x: 48.1 mm | y: 96.3 mm | z: 47.9 mm |

The displacement vectors for the three points can be calculated and used to determine the axis of helical motion, i.e., the helical-shaped distraction path. The axis of the helical-shaped distraction path can be found in two steps. The system will first determine the orientation of the helical axis, then its location. After the helical axis has been established, the algorithm calculates the angular displacement (rotation) about the helical axis, and then, the translation along the axis, for each moving segment.

FIG. 35 illustrates an example user display and results of determined helical axis of motion for the example provided above in Tables 1 and 2. The coordinates of the spiral axis unit direction are (−0.988, 0.087, −0.124) and the axis point is identified as (34.002, 52.163, 124.997), where the pitch of the helical-shaped path is −4.22. The distraction path translates −1.041 mm along the axis of the helical-shaped distraction path and rotates 14.1-degrees around the helix.

After the parameters of motion have been calculated, the system can animate the movement of the bone segments (and teeth) as they follow their path of motion. It is contemplated that the system can draw paths of motion for any identified point/marker on the various bone segments. Likewise, the length of each path can be calculated to determine the distraction velocities at different bone locations. Possible collisions between the various bone segments can be mapped, and likewise the Boolean volumes of intersection between bone segments, across their path of motion can be calculated. By mapping the collision and volumes of intersection, the operator can identify where the various bone segments need to be modified (i.e., trimmed) during the procedure.

Figure 36B:
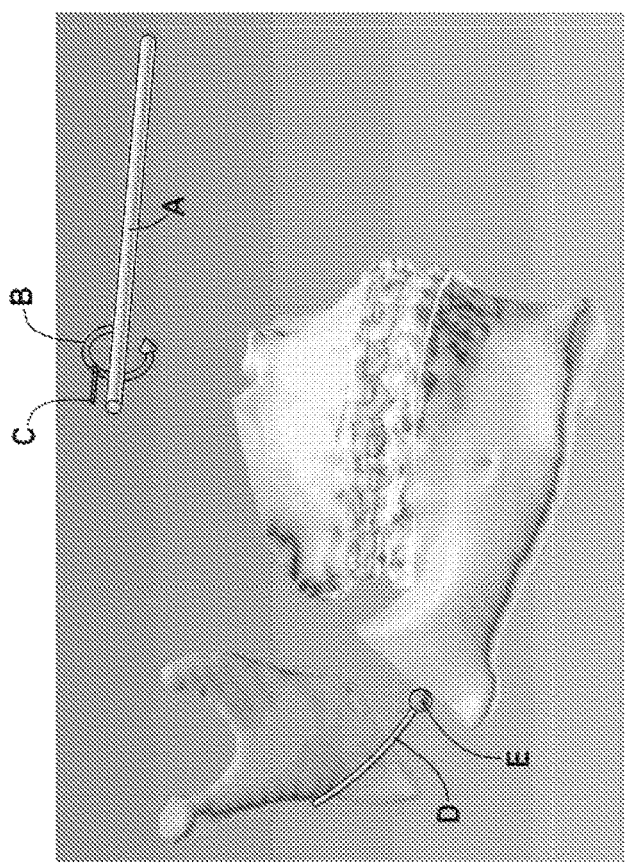
FIG. 36B is a portion of an example graphical user interface with the patient model in the final/desired alignment.
Figure 36A:
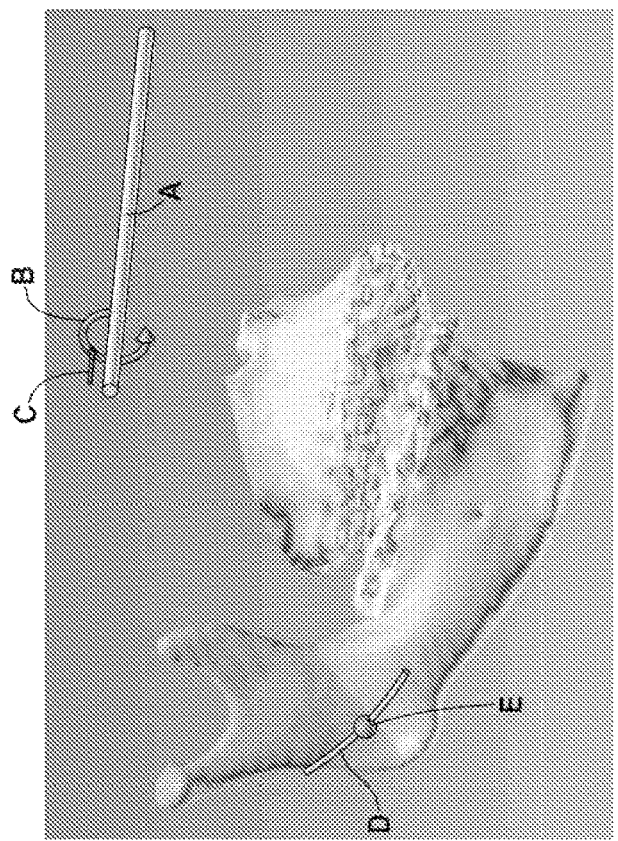
FIG. 36A is a portion of an example graphical user interface with the patient model in the initial alignment.

FIGS. 36A and 36B are portions of an example user display illustrating the helical motion of the second bone segment along the distraction path. FIG. 36A shows the original alignment of the bone segment model and FIG. 36B shows the final/desired alignment of the patient model. The axis of the helical distraction path is identified as Axis A, arrow B identifies the direction of angular displacement of the helical-shaped distraction path, and arrow C identifies the direction of linear displacement, curve D identifies the distraction path such that any point (such at point E) and any point on the second bone segment (front part of the lower jaw) move along the helical-shaped distraction path.

In the fourth step, distractor design, the various components of the custom distractor 100 are modeled and created. As discussed above, all distractors 100 include at least a steering apparatus (inner member/outer sleeve, rail member/carriage member), an anchoring member for attaching the distractor to the bone segments, and the driving mechanism (e.g., worm gear, flexible screw). To design the distractor components, the basic features of the distractor and the device location are provided to the system. For example, the operator may identify the cross-sectional area and/or shape of the outer sleeve/rail. The operator may also identify any desired lengthening of the outer sleeve/rail need beyond what is calculated as needed for the distraction movement. The user may also provide the cross-sectional area and/or shape of the inner member/carriage(s) and any constraint to the length of the inner member/carriage, or any desired lengthening of the carriage beyond what the computer calculates as needed for the distraction movement. The operator may also provide the starting position of the inner member/carriage along the distraction path. The operator may also provide an extension/increased length of the outer sleeve/rail member and/or inner member/carriage members. The operator may also identify an offset of the distractor from the bone surface.

Figure 37:
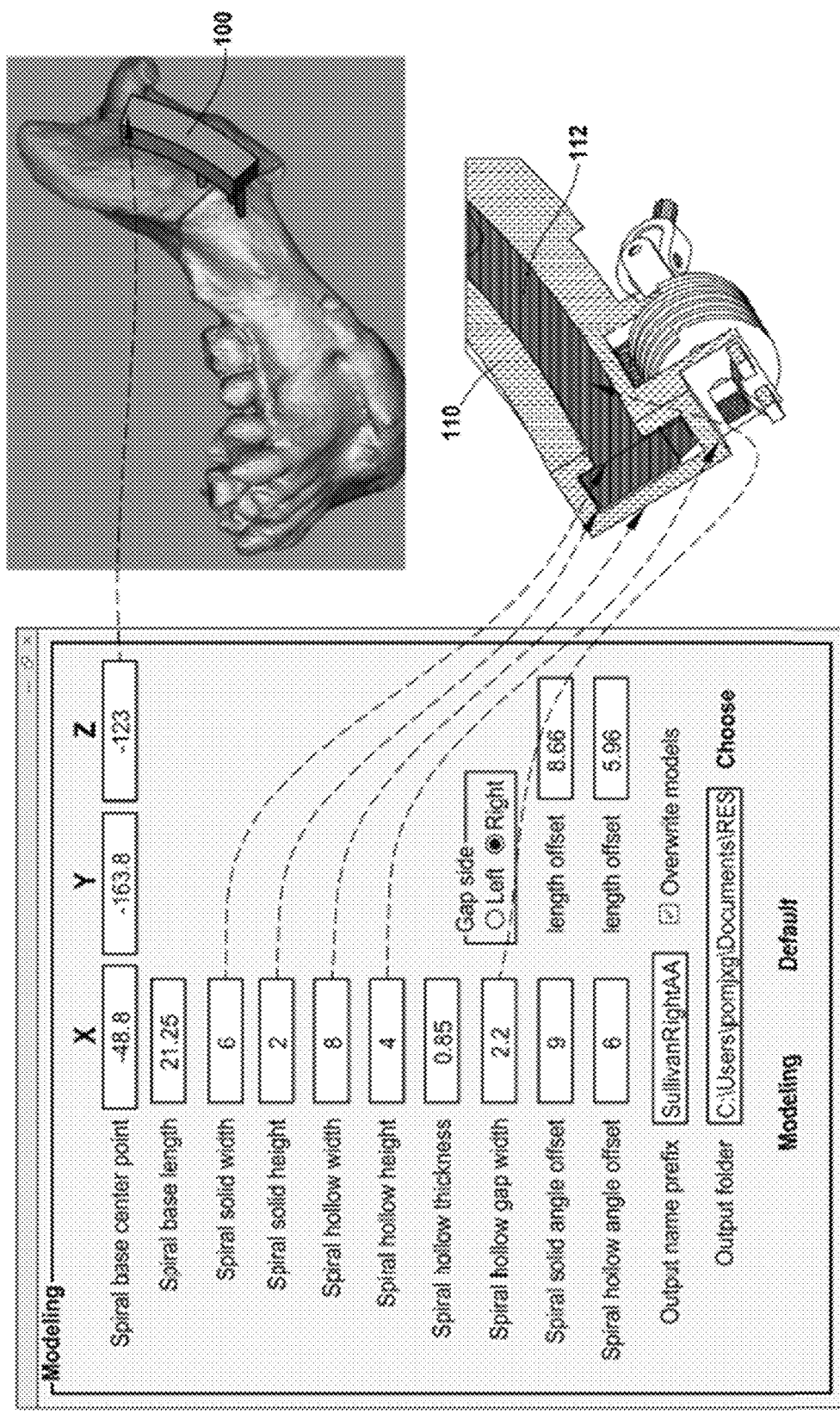
FIG. 37 is a portion of an example graphical user interface.

FIG. 37 illustrates an example user display and identifies the correlation between the operator provided data and the custom distraction device. The spiral base center point identifies the location of the base of the distractor 100. The spiral base length identified the length of the distractor 100. The spiral solid width corresponds to the inside edge of the inner member 112. The spiral solid height corresponds to the top edge of the inner member 112. The spiral hollow width corresponds to the outside edge of the outer sleeve 110. The spiral hollow height corresponds to the bottom edge of the outer sleeve 110. The spiral hollow gap width corresponds to the back surface of the distractor Based on the calculated (custom) helical-distraction path and the operator entered distractor data, a custom three-dimensional model (e.g., CAD file) of the distractor is created, where the custom distractor includes a steering apparatus (inner member/outer sleeve, rail member/carriage member), an anchoring member for attaching the distractor to the bone segments, and the driving mechanism (e.g., worm gear, flexible screw).

To create the three-dimensional model, the system can set a two-dimensional cross-section of the outer sleeve/rail member at the origin of the distraction path and align the shape orthogonally to the path. Next, the distraction path is lengthened by a predetermined about (e.g., an amount determined by the operator). The system then lofts the two-dimensional shape along the distraction path, creating a three-dimensional outer sleeve/rail member. The lofted object is triangulated and can be saved as an STL file, or in any other file format the manufacturing device (e.g., milling machine or 3D printer) may require.

To design the custom-carriage, the system sets the two-dimensional cross-section of the inner member/carriage at the tail of the distraction path and aligns the shape orthogonally to it. The two-dimensional shape is then positioned along the distraction path at the starting position of the inner member/carriage. The distraction path is limited or extended by the amount selected by the operator. The two-dimensional image is then lofted along the distraction path, creating a three-dimensional curved inner member/carriage. The lofted object is triangulated and is saved as an STL file, or any other file format the manufacturing device (e.g., milling machine or 3D printer) may require.

Figure 38A:
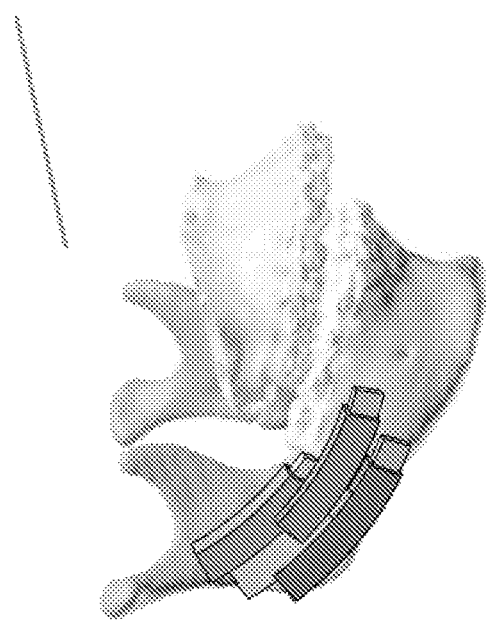
FIG. 38A is a perspective view of an anatomical model including multiple distraction devices where the patient's anatomy is illustrated in an initial alignment.
Figure 38B:
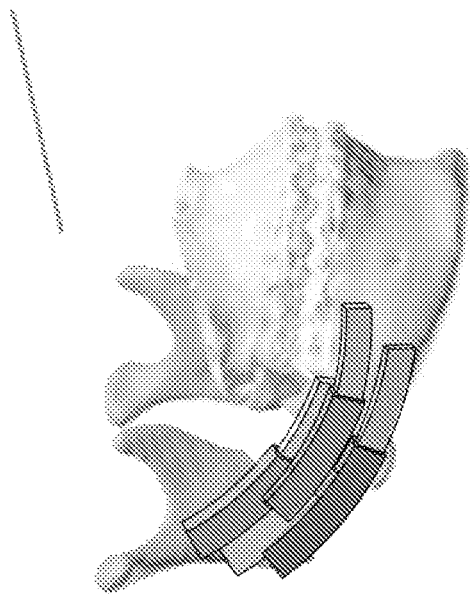
FIG. 38B is a perspective view of an anatomical model including multiple distraction devices where the patient's anatomy is illustrated in a final/desired alignment.

Once the outer sleeve/rail and inner member/carriage is created, they are then displayed to the operator along with the patient's anatomic model. Rendering the distraction device together with the bones, teeth, nerves and soft-tissue helps surgeons assess the adequacy of the device. The ideal distraction device may require a different location that the one picked initially. Thus, the system supports the design of multiple custom devices. FIGS. 38A and 38B illustrate a patient model including multiple possible (custom) distraction devices. Operators may wish to try different device locations or different device types/shapes. Using the present system, they are able to move the distractor to a new location and immediately after the new location is entered, the system will create a new outer sleeve/rail and inner member/carriage. Importantly, the operator must understand that each different device location will generate a different distractor. During distraction, all the moving points rotated about a fixed axis, the axis of the helical-shaped distraction path. Points located at different distances from the rotation axis follow different distraction paths, as such, a new/different distractor located at a different position on the patient will have different structure/shape.

The operator can also try different device configurations. For this, the operator may enter new device parameters, or selects a new device from a library of previously created distraction devices. By displaying multiple devices on the same patient model, the operator is able to assess their different options. It is contemplated that the system will also let the operator hide any devices, to unclutter the scene.

In addition to the custom outer sleeve/rail and inner member/carriage created by the system, the present system can also a distractor also design custom anchoring members/ footplates. As described above the anchoring members/ footplates secure the distractor to the bone. To design the custom anchoring members/footplate, the operator will identify the ideal screw positions for each anchoring members/ footplate. The screws must be at a minimal distance from the osteotomy and should avoid teeth and nerves. The present system can render the bones in translucent material to show these structures and simulate screw insertion by installing cylinders that have the same length and diameter as the screws. Using the identified screw locations and bone surface shape data, custom anchoring members/footplates are designed.

Figure 39:
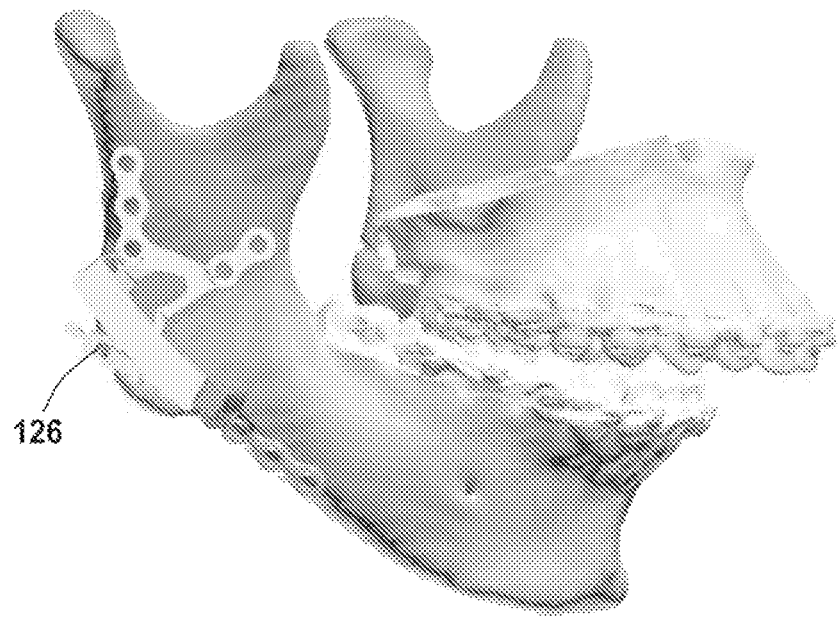
FIG. 39 is a perspective view of an anatomical model including an example distraction device where the patient's anatomy is illustrated in an initial alignment.

Using the present system, the operator can also identify the ideal exit point of the activation arm. For example, a mandibular distractor could have an activation arm that exits the face below the ear, above the ear, or through the mouth. When one designs a custom device, it is important to know ahead of time where the activation arm will exit the face, for this location determines the ideal location and orientation of the activating mechanism. See, for example, the extension arm 126 location on the example distractor and patent model depicted in FIG. 39.

Figure 40:
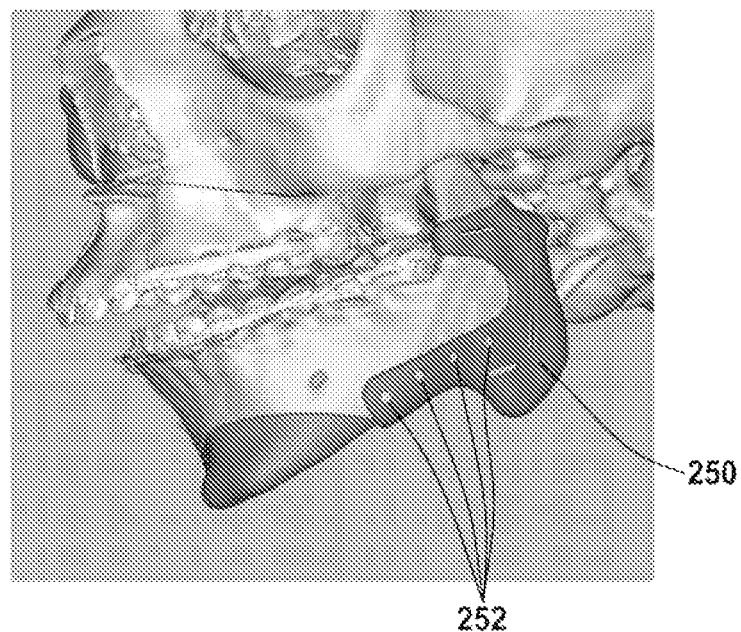
FIG. 40 is a perspective view of an anatomical model include a pilot hole template.

Because custom distractors are specific to each patient, and to their location within the patient, it is important that the surgeon can virtually install the distractor in the exact position for which they were designs. Misalignment will hinder treatment outcomes and cause patient discomfort. To ensure exact placement, the present system can be used to create templates for locating the pilot holes for screws used to secure the anchoring members/footplates to the bone segments. Using the model data known about the screw location and patient anatomy, a model of the template is created identifying the locations of the attachment screws. The model is saved as an STL file, or any other file format the manufacturing device (e.g., milling machine or 3D printer) may require. Using the model, the template is created. As illustrated in FIG. 40, during installation of the distractor, the template 250 is placed adjacent to the patient's and the pilot holes 252 are drilled at the desired location on the bone segment.

Figure 41:
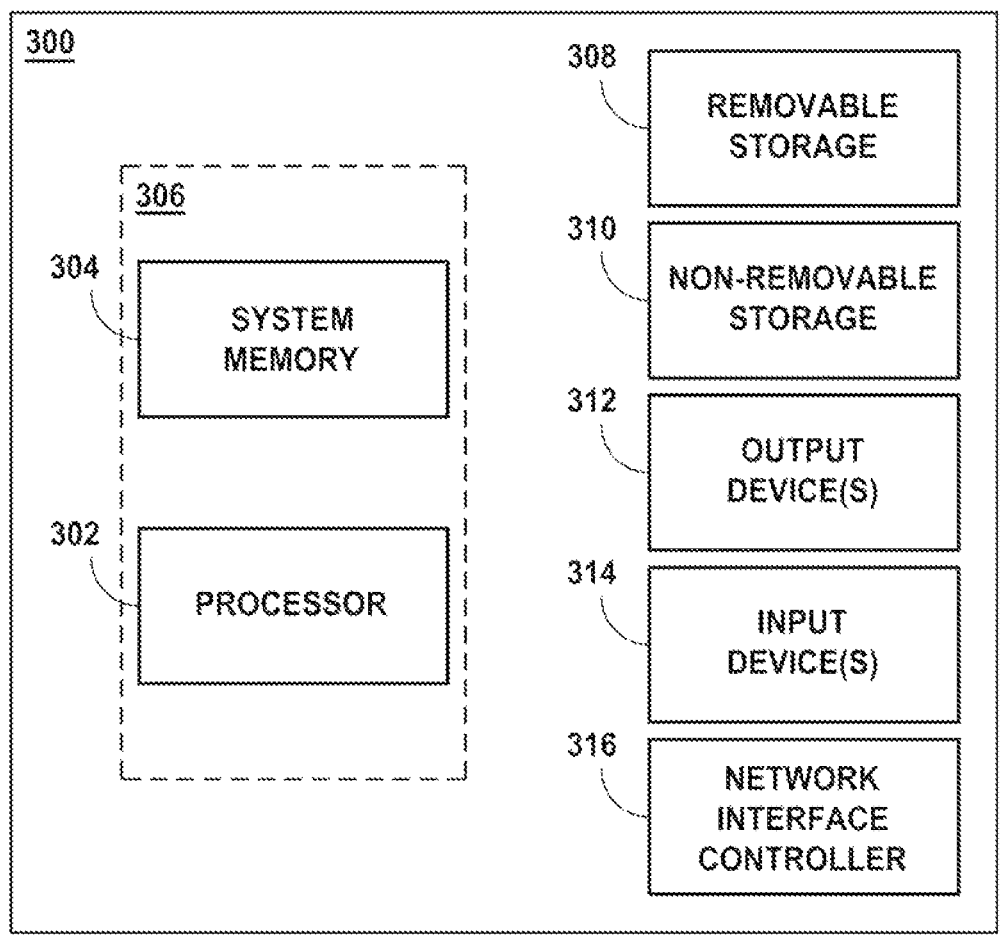
FIG. 41 is a schematic view of an exemplary processing unit.

In some implementations, the system can include a processing unit 300 to implement computer instructions/logic for designing the custom craniofacial distraction devices (and pilot templates) and creating models of the same. When the logical operations described herein are implemented in software, the process may execute on any type of computing architecture or platform. For example, the functions of the design system may be implemented on any type of computing architecture or platform. The implementation shown in FIG. 41 illustrates an example computing device/processing unit 300 upon which implementations disclosed herein may be implemented. The processing unit 300 can include a bus or other communication mechanism for communicating information among various components of the processing unit 300. In its most basic configuration, processing unit 300 typically includes at least one processor 302 and system memory 304. Depending on the exact configuration and type of computing device, system memory 304 may be volatile (such as random access memory (RAM)), non-volatile (such as read-only memory (ROM), flash memory, etc.), or some combination of the two. This most basic configuration is illustrated in FIG. 41 by a dashed line 406. The processor 302 may be a standard programmable processor that performs arithmetic and logic operations necessary for operation of the processing unit 300.

The processing unit 300 can have additional features/ functionality. For example, the processing unit 300 may include additional storage such as removable storage 308 and non-removable storage 310 including, but not limited to, magnetic or optical disks or tapes. For example, the processing unit 300 may be configured for storing at least a portion of the input data (e.g., patient models, operator input) and the created models (distractor, pilot hole templates) to one or more of the storage 308, 310. In one implementation, the input data and created models (or a portion thereof) may be stored on the non-removable storage 310 to keep the data secure. In addition, the input data and created models may be stored and/or transmitted in full or as a set of data related to portions of the input data and created models.

The processing unit 300 can also contain network connection(s) via a network interface controller 316 that allow the device to communicate with other devices, such as a CAT scan, X-ray machine, 3D printer, or milling machine. The processing unit 300 can also have input device(s) 314 such as a keyboard, mouse, touch screen, antenna or other systems configured to communicate with the system memory 304 and processor 302. Output device(s) 312 such as a display, speakers, printer, etc. may also be included. The additional devices can be connected to the bus in order to facilitate communication of data among the components of the processing unit 300.

The processor 302 can be configured to execute program code encoded in tangible, computer-readable media. Computer-readable media refers to any media that can provide data that causes the processing unit 300 (i.e., a machine) to operate in a particular fashion. Various computer-readable media can be utilized to provide instructions to the processor 302 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an exemplary implementation, the processor 302 can execute program code stored in the system memory 304. For example, the bus can carry data to the system memory 304, from which the processor 302 receives and executes instructions. The data received by the system memory 304 can optionally be stored on the removable storage 308 or the non-removable storage 310 before or after execution by the processor 302.

The processing unit 300 typically includes a variety of computer-readable media. Computer-readable media can be any available media that can be accessed by the processing unit (300) and includes both volatile and non-volatile media, removable and non-removable media. Computer storage media include volatile and non-volatile, and removable and non-removable media implemented in any method or technology for storage of information such as computer readable instructions, data structures, program modules or other data. System memory 304, removable storage 308, and non-removable storage 310 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by the processing unit 300. Any such computer storage media can be part of the processing unit 300.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the following claims.

What is claimed is:

1. An orthopedic distraction device comprising:
   a steering apparatus including
      an outer sleeve defining a helical-shaped distraction path, and
      a telescoping inner member coupled to the outer sleeve for movement along the helical-shaped distraction path;
   a first anchoring member coupled to the outer sleeve and configured to anchor to a first bone segment;
   a second anchoring member coupled to the telescoping inner member and configured to anchor to a second bone segment; and
   a distraction drive mechanism driving movement of the steering apparatus along the helical-shaped distraction path;
   wherein the telescoping inner member is movable along the helical-shaped distraction path relative to the outer sleeve to create a gap between the first bone segment and the second bone segment.

2. The device of claim 1, wherein the distraction drive mechanism includes at least one of a worm-rack drive, flexible wires, friction ratchet mechanism, and a hydraulic mechanism.

3. The device of claim 2, wherein the distraction drive mechanism comprises a worm-rack drive including:
   a worm gear rotatably coupled to the outer sleeve, the worm gear threadably coupled to a toothed surface provided on the telescoping inner member,
   wherein rotation of the worm gear causes the telescoping inner member to move along the helical-shaped distraction path.

4. The device of claim 3, wherein the worm-rack drive is positioned on one of an inferior, superior, lateral, or medial surface of the steering apparatus.

5. The device of claim 3, wherein an activation port of the distraction drive mechanism is coupled to the worm gear, the activation port for receiving rotational input forces to drive the rotation of the worm gear.

6. The device of claim 5, further comprising an extension arm coupled to the activation port, rotation of the extension arm provides the rotational input forces to the distraction drive mechanism and results in a corresponding driving movement of the steering apparatus along the helical-shaped distraction path,
   wherein the extension arm is sized and configured to extend through a patient's skin or oral mucosa.

7. The device of claim 6, wherein the extension arm is coupled to the activation port at a universal joint-type coupling.

8. The device of claim 3, wherein the worm-rack drive includes an anti-rotation mechanism for limiting rotational movement of the worm gear, the anti-rotation mechanism comprising:
   a locking member, and an engaging member, wherein engagement between the locking member and the engaging member is configured to the rotational movement of the worm gear.

9. The device of claim 8, wherein the engaging member comprises a compliant material that limits rotational movement of the locking member, where the compliant material allows the rotational movement of the locking member provided at a rotational force below a threshold resistive force of the engaging member.

10. The device of claim 9, wherein the engaging member comprises a bow spring.

11. The device of claim 9, wherein the locking member comprises a non-circular-shape in cross-section.

12. The device of claim 1, wherein the distraction drive mechanism comprises a flexible screw extending within the telescoping inner member and rotatably coupled to the outer sleeve,
wherein the flexible screw is threadably coupled to the telescoping inner member and rotates freely with respect to the outer sleeve, such that rotation of the flexible screw causes the telescoping inner member to translate along the outer sleeve.

13. The device of claim 12, wherein a threaded opening at a proximal end of the telescoping inner member engages threads of the flexible screw, such that the rotation of the flexible screw causes the telescoping inner member to translate along the outer sleeve.

14. The device of claim 12, wherein a proximal end of the flexible screw includes a shoulder for rotatably engaging an opening at a proximal end of the outer sleeve.

15. The device of claim 12, wherein an activation port of the distraction drive mechanism is coupled to a proximal end of the flexible screw, the activation port extending from a proximal end of the outer sleeve, the activation port for receiving rotational input forces to drive the rotation of the flexible screw.

16. The device of claim 15, further comprising an extension arm coupled to the activation port, rotation of the extension arm the rotational input forces that result in the rotation of the flexible screw,
wherein the extension arm is sized and configured to extend through a patient's skin or oral mucosa.

17. The device of claim 16, wherein the extension arm is coupled to the activation port at a universal joint-type coupling.

18. The device of claim 1, wherein the telescoping inner member extends from a distal opening provided on the outer sleeve,
wherein the movement of the telescoping inner member and the outer sleeve along the helical-shaped distraction path causes the telescoping inner member to further extend from the distal opening of the outer sleeve.

19. The device of claim 1, wherein the steering apparatus further includes an intermediate sleeve extending between the outer sleeve and the telescoping inner member, the intermediate sleeve extending from a distal opening provided in the outer sleeve and the telescoping inner member extending from a distal opening provided in the intermediate sleeve,
wherein the movement of the steering apparatus along the helical-shaped distraction path causes the intermediate sleeve to further extend from the distal opening of the outer sleeve and causes the telescoping inner member to further extend from the distal opening of the intermediate sleeve.

20. The device of claim 1, wherein the outer sleeve and the telescoping inner member define a generally rectilinear cross-sectional shape.

21. The device of claim 1, wherein the outer sleeve and the telescoping inner member define a generally circular cross-sectional shape.

22. The device of claim 1, wherein the first anchoring member includes a first footplate configured to couple the outer sleeve to the first bone segment and the second anchoring member includes a second footplate configured to couple the telescoping inner member to the second bone segment.

23. The device of claim 22, wherein the first and second footplates are sized and shaped to correspond to respective surfaces of the first and second bone segments.

24. The device of claim 23, wherein each of the first and second footplates include an opening configured to receive a bone screw to fix the first and second footplates to the first and second bone segments, respectively,
wherein a location of each of the openings is predetermined and configured to lay over a respective portion of the first and second bone segments having an increased thickness and avoiding a blood vessel, nerve, and tooth.

25. The device of claim 1, wherein the helical-shaped distraction path defines a path of movement configured to inhibit pathological condylar displacement between the first and second bone segments.

26. The device of claim 1, wherein at least one of the outer sleeve and the telescoping inner member are movable along the helical-shaped distraction path between a first position of the first and second bone segments and a second position of the first and second bone segments.

27. The device of claim 26, wherein the second position of the first and second bone segments identifies a predetermined re-aligned position of the first and second bone segments.

* * * * *

UNITED STATES PATENT AND TRADEMARK OFFICE
CERTIFICATE OF CORRECTION

PATENT NO. : 12,207,850 B2
APPLICATION NO. : 17/298171
DATED : January 28, 2025
INVENTOR(S) : Jaime Gateno Page 1 of 1

It is certified that error appears in the above-identified patent and that said Letters Patent is hereby corrected as shown below:

In the Claims

In Column 29, Lines 2-3 of Claim 8, "...engaging member is configured to the rotational movement of the worm gear." should read -- engaging member is configured to inhibit the rotational movement of the worm gear. --

In Column 29, Lines 38-39 of Claim 16, "...rotation of the extension arm the rotational input forces that..." should read -- rotation of the extension arm provides the rotational input forces that --

Signed and Sealed this
Twenty-seventh Day of May, 2025

Coke Morgan Stewart
*Acting Director of the United States Patent and Trademark Office*